United States Patent [19]
Tolkoff et al.

[11] Patent Number: 5,637,102
[45] Date of Patent: Jun. 10, 1997

[54] DUAL-TYPE CATHETER CONNECTION SYSTEM

[75] Inventors: M. Joshua Tolkoff, Brookline; Robert C. Allman, Wakefield, both of Mass.; Kenneth A. Eliasen, Murray, Utah; Robert N. Gailey, Farmington, Utah; Kelly J. Christian, Sandy, Utah; Donald J. Jones, West Valley City, Utah

[73] Assignee: C. R. Bard, Inc., Murray Hill, N.J.

[21] Appl. No.: 449,210

[22] Filed: May 24, 1995

[51] Int. Cl.$^6$ .................................................. A61M 25/00
[52] U.S. Cl. ........................................... 604/283; 285/417
[58] Field of Search ................................. 604/283, 285, 604/264, 265, 49; 285/417, 338

[56] References Cited

U.S. PATENT DOCUMENTS

| | | | |
|---|---|---|---|
| 2,704,074 | 3/1955 | Butler | 128/221 |
| 4,511,163 | 4/1985 | Harris et al. . | |
| 4,564,222 | 1/1986 | Loker et al. | 285/243 |
| 4,592,749 | 6/1986 | Ebling et al. . | |
| 4,630,847 | 12/1986 | Blenkush . | |
| 4,790,832 | 12/1988 | Lopez . | |
| 4,826,477 | 5/1989 | Adams . | |
| 4,863,439 | 9/1989 | Sanderson . | |
| 4,878,900 | 11/1989 | Sundt . | |
| 4,929,236 | 5/1990 | Sampson . | |
| 4,969,879 | 11/1990 | Lichte . | |
| 5,026,344 | 6/1991 | Dijkstra et al. . | |
| 5,045,060 | 9/1991 | Melsky et al. . | |
| 5,049,139 | 9/1991 | Gilchrist . | |
| 5,129,891 | 7/1992 | Young . | |
| 5,137,529 | 8/1992 | Watson et al. | 604/891.1 |
| 5,180,365 | 1/1993 | Ensminger et al. . | |
| 5,312,337 | 5/1994 | Flaherty et al. . | |
| 5,356,381 | 10/1994 | Ensminger et al. . | |
| 5,360,407 | 11/1994 | Leonard . | |
| 5,360,418 | 11/1994 | Weilbacher et al. . | |
| 5,387,192 | 2/1995 | Glantz et al. . | |
| 5,399,168 | 3/1995 | Wadsworth, Jr. et al. . | |
| 5,405,339 | 4/1995 | Kohnen et al. . | |

FOREIGN PATENT DOCUMENTS

| | | | |
|---|---|---|---|
| 0343910 | 11/1989 | European Pat. Off. | 05/14 |
| 537892 | 4/1993 | European Pat. Off. . | |
| 2703593 | 4/1993 | France . | |
| 2703593 | 10/1994 | France | 39/37 |
| 1933802 | 2/1970 | Germany | 17/2 |
| 2949315 | 12/1979 | Germany . | |
| 2949315 | 7/1980 | Germany | 16/33 |
| 1269405 | 6/1969 | United Kingdom . | |
| 2257764 | 1/1993 | United Kingdom . | |

*Primary Examiner*—Robert A. Hafer
*Assistant Examiner*—Perry E. VanOver
*Attorney, Agent, or Firm*—Trask Britt & Rossa

[57] ABSTRACT

A catheter connection system is defined by a rigid, tubular stem attached at a proximal end thereof to a medical device. The stem has a plurality of comparably configured engagement barbs encircling and radially, outwardly extending on an exterior surface of the stem. A locking barb also encircles and radially, outwardly extends on the surface of the stem between the medical device and the engagement barbs. A rigid first locking sleeve is provided for inwardly compressing a portion of a body wall of a silicone catheter against the locking barb on the stem when the stem is received in the lumen of the silicone catheter to create a mechanical joinder and liquid-tight seal between the silicone catheter and the stem. In the alternative, a compression sleeve housed within a rigid second locking sleeve is provided for compressing a body wall of a polyurethane catheter against the engagement barbs on the stem to create a mechanical joinder and liquid-tight seal between the polyurethane catheter and the stem.

119 Claims, 13 Drawing Sheets

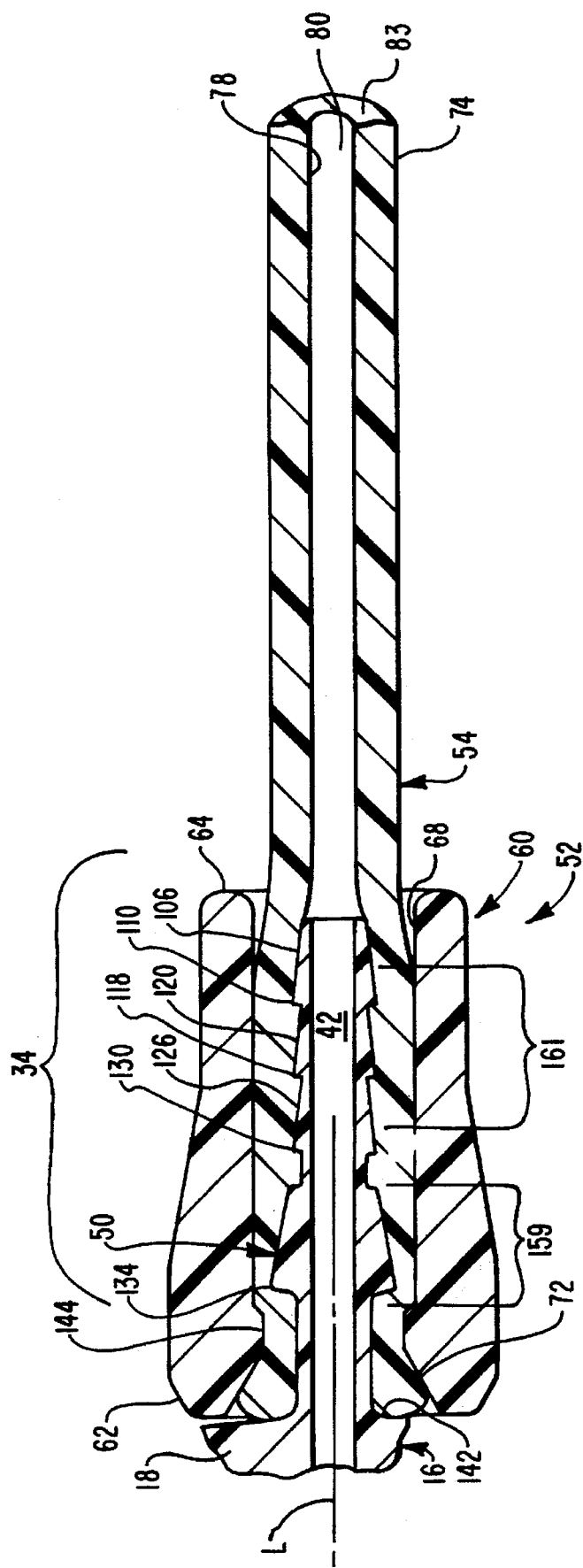

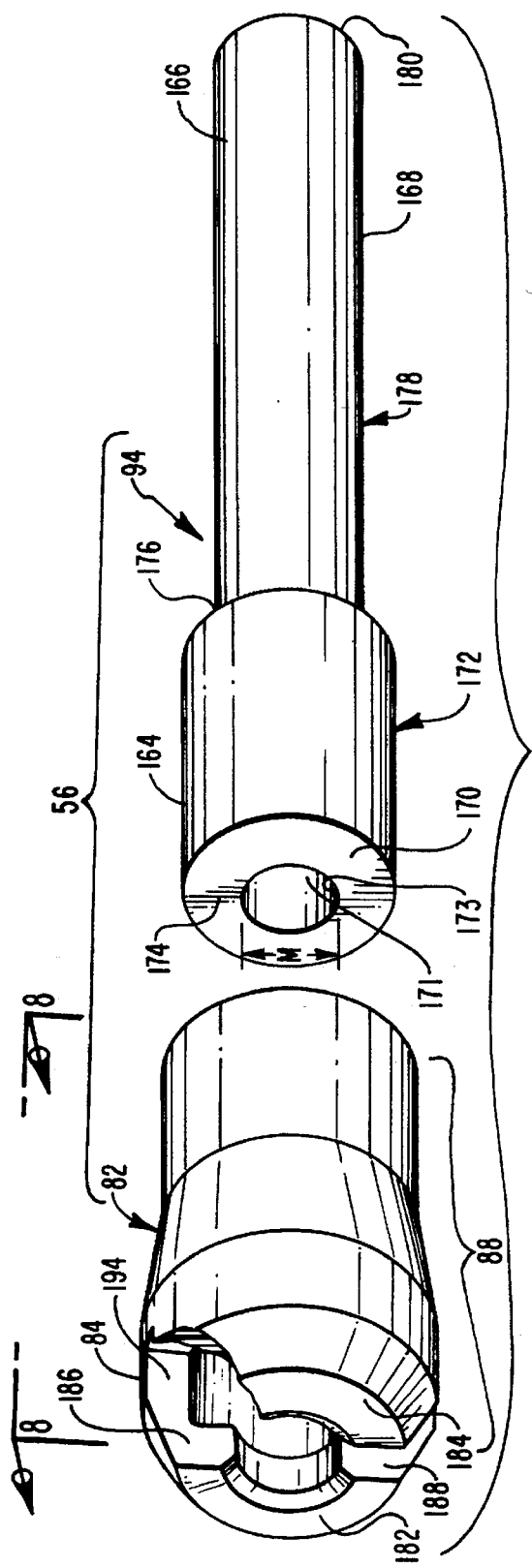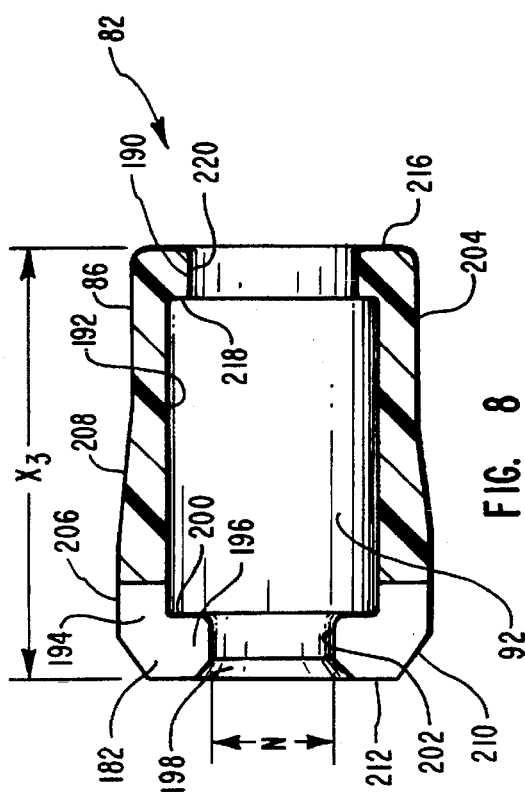

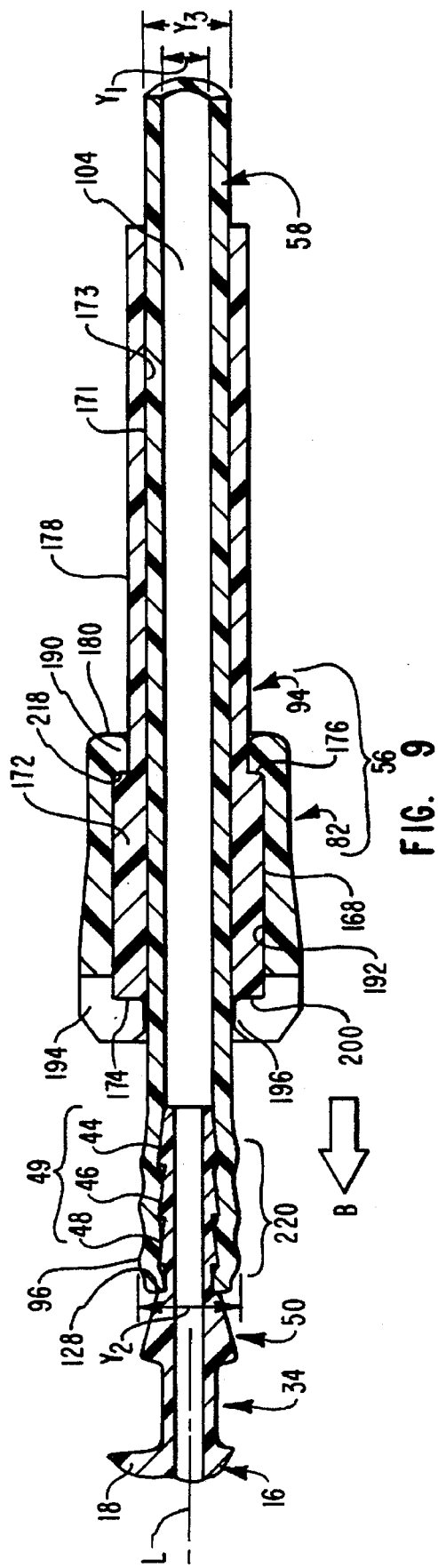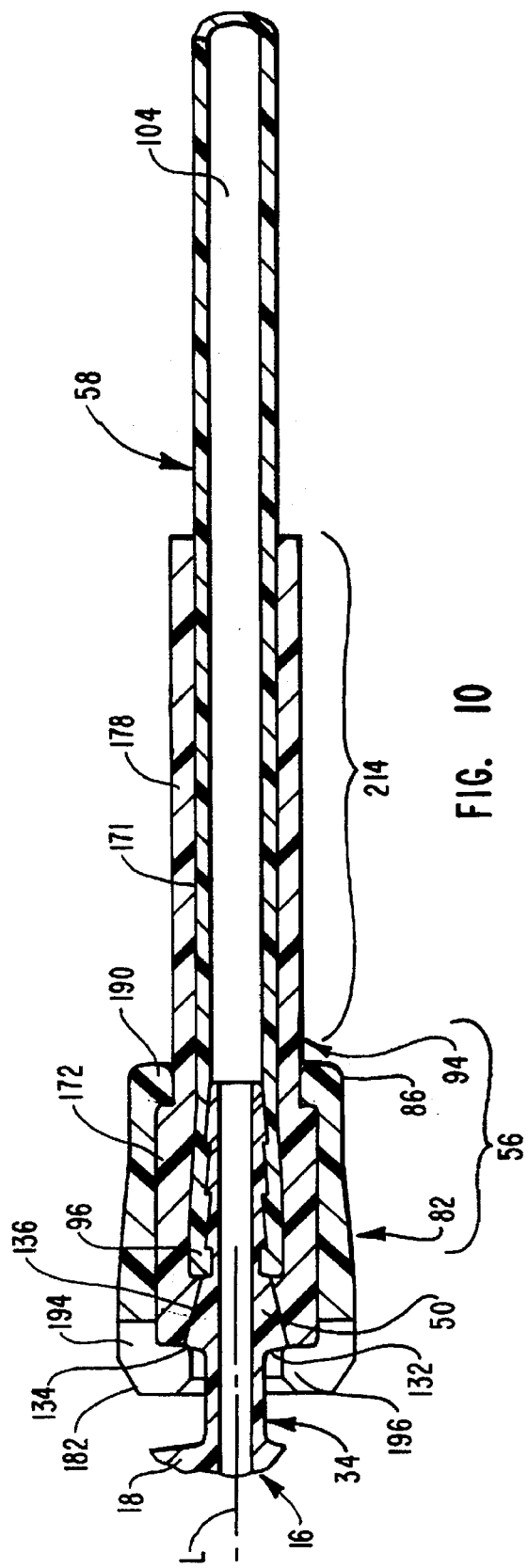

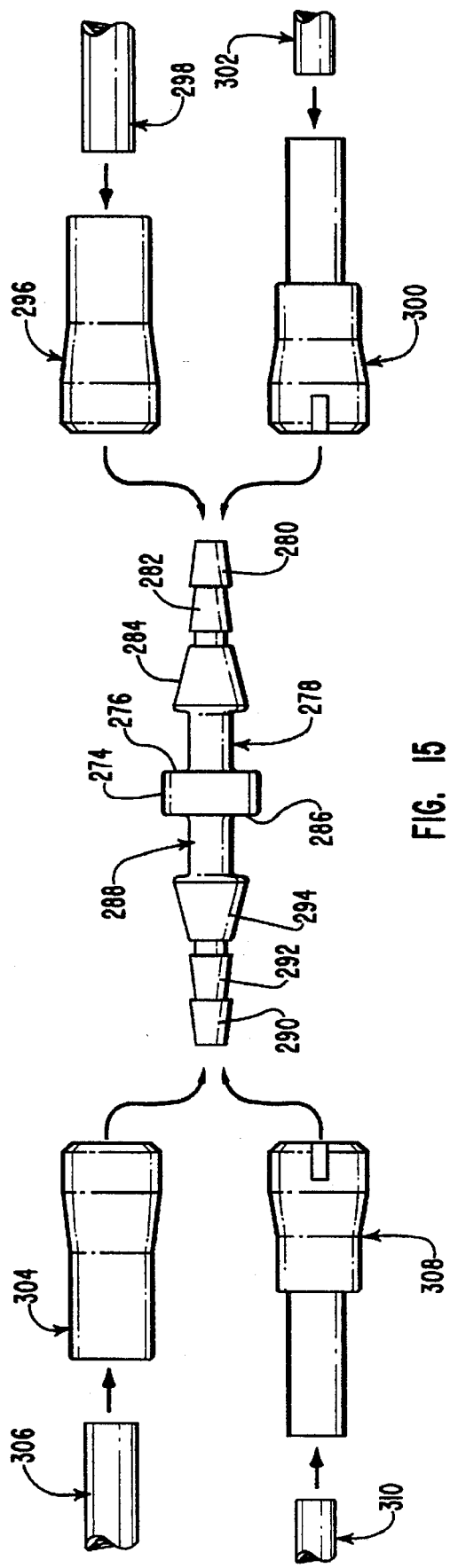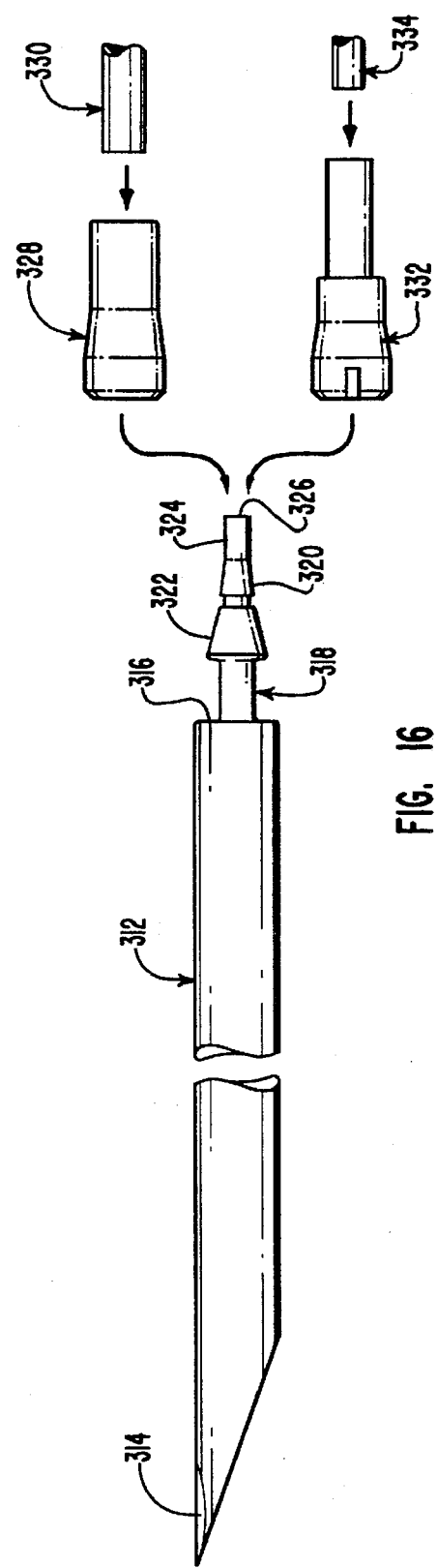
FIG. 15
FIG. 16

DUAL-TYPE CATHETER CONNECTION SYSTEM

BACKGROUND OF THE INVENTION

1. The Field of the Invention

The present invention relates to systems for attaching flexible catheters to medical devices.

2. Background Art

Catheters are used extensively in the medical field to facilitate the performance of recurrent therapeutic tasks inside the body of patients.

For example, using only a relatively small incision, a catheter can be implanted in the body of a patient and used to deliver fluid directly to a predetermined location, either within the cardiovascular system, the peritoneal cavity, or some organ, such as the stomach, the heart, the liver, the brain, or the reproductive tract. Alternatively or in addition thereto, such implanted catheters can be used to periodically sample from these locations, to drain fluids to relieve pressure, to withdraw fluids for extracorporeal processing on an ongoing basis, or to monitor internal body conditions, such as pressure, temperature, or fluid flow rates.

Catheters are, however, fabricated in various structural configurations, depending upon the intended use for each.

A common catheter design used in performing many of the procedures mentioned above includes an elongated, flexible cylindrical catheter body having a fluid flow passageway or a lumen extending along the interior of that catheter body. During use, an end of the catheter referred to as the distal end is inserted into the body of the patient through an incision or a body orifice and then entered into a body cavity or internal passageway, such as a blood vessel in the cardiovascular system. The distal end of the catheter is advanced within the body cavity or along the internal passageway until the distal end is located at a desired predetermined location for conducting an intended therapeutic activity. Fluid containing medication, nutrients, or cleansing agents can then be introduced through the lumen of the catheter and delivered at the predetermined location through the distal end of the catheter.

The end of such a catheter opposite the distal end is referred to as the proximal end. Once the distal end of a catheter has been implanted at a predetermined location as described above, the proximal end must be attached to the type of medical device that is appropriate to the specific task and manner of use to which the implanted catheter is to be applied. On some occasions the distal end of the catheter with the attached medical device remains outside the body of the patient. In other situations both are implanted subcutaneously in the body of the patient.

For example, if the proximal end of an implanted catheter is to remain outside the body of the patient, the proximal end of the catheter is frequently attached to a catheter termination device that facilitates access to the lumen by a hypodermic needle. Commonly, such catheter termination devices also function to close the proximal end of the catheter when the infusion or withdrawal of fluid is not taking place. In some circumstances the proximal end of an implanted catheter may need to be coupled to tubing that allows the proximal end of the catheter to in turn be fluid coupled to sizable medical devices that must remain outside the body of the patient. In such circumstances the catheter termination device to which the proximal end of the catheter is coupled is ideally selectively and non-destructively couplable with tubing, but the catheter termination device is also provided with the capacity to close the proximal end of the associated catheter whenever such tubing is detached.

On occasion the proximal end of the catheter is attached to one side of a fluid flow accommodating structure that has on the other side structures appropriate for coupling to yet another catheter. This may be done to increase the length of a catheter that is already implanted, or to splice the broken proximal end of an implanted catheter.

In some instances, the proximal end of an implanted catheter will be attached to an access device that is itself also implantable in the body of a patient. Then the entirety of the catheter with the access device attached thereto is embedded at appropriate locations in the tissue of the patient with the distal end of the catheter disposed at the predetermined location at which therapeutic activity is to be effected. Under such circumstances, medication is then delivered to the lumen of the catheter, or withdrawn therefrom, utilizing a hypodermic needle that penetrates the skin of the patient at the implantation site of the access structure and effects a fluid coupling with that access structure.

One problem encountered in attaching the proximal end of a catheter to a given medical device is that catheters are fabricated from a variety of different materials. These materials vary in material properties, such as tensile strength, shear strength, flexibility, and compressibility. Some materials tend to relax over time after being stretched over a rigid structure, a property referred to as creep, while others do not. Some kink more easily than others. Some shear easily in specific directions, while others resist such structural failures.

Silicone and polyurethane are materials used extensively in the medical field in the manufacture of implantable catheters. Silicone and polyurethane each have unique material properties. The use of one material over the other is usually determined by the intended use of the catheter and the conditions in the body to which the catheter will as a result be exposed. Often the selection of a catheter of one material over a catheter of another material is to a large degree merely a function of availability or of the preferences and prior experience of the medical personnel who will use the catheter selected.

The different materials from which catheters can be fabricated results in the availability of catheters having dramatically different material properties.

One area in which different material properties in catheters can have a significant impact is the behavior of the catheter in relation to the catheter attachment structures used to secure the proximal end of a catheter to a medical device. Some types of catheter attachment structures are inappropriate, or even dangerous, when used in connection with catheters made of a particular material. In many cases a specific catheter attachment structure is appropriate, or even safe, only when used with catheters made of a single, specific material.

Catheter attachment structures may cut, tear, or shear catheters of one material, while functioning with absolute safety relative to catheters made of another. One catheter attachment structure may be unable to effect a secure mechanical connection or a fluid tight seal relative to a given catheter material, while performing with adequate safety in relation to another catheter material. One catheter material may be incapable of cooperating effectively with the elements of a given catheter attachment structure, while being ideally suited to doing so with the elements of a different catheter attachment structure.

Thus, if a medical facility intends to permit its personnel to utilize catheters made from a selection of different materials, these facilities must correspondingly purchase and maintain an inventory of corresponding, appropriate catheter attachment structures for each type of catheter material.

Some brands of medical devices are manufactured with components of only a single type of catheter attachment system secured thereto. Thus, the freedom of medical practitioners to select among catheters made of different materials is limited in some cases by the brand of the medical device that is intended to be used in the procedure. Under such circumstances, the freedom to select differing catheter materials is in fact illusory, unless several brands of a given medical device are kept on hand at a medical facility.

In most instances at least one component of each catheter attachment structure is permanently secured to the medical device to which a catheter is to be coupled. Thus, the selection of one catheter attachment system frequently implies the selection of a corresponding medical device. An inventory of differing catheter attachment systems can, therefore, require in reality an inventory of different medical devices.

Naturally, there are costs associated with such enterprises.

The purchase of different catheter attachment structures and several brands of a given type of medical device is expensive and requires a commitment of space to store an inventory. Once these costs are assumed, however, the availability of a variety of catheter attachment structures and a plurality of brands of medical devices at a medical facility will afford the medical personnel the freedom to use catheters fabricated from a variety of materials.

There are, however, risks associated with such practices. The availability of a plurality of types of catheter attachment structures can complicate medical procedures by requiring close attention to the correlation of an appropriate catheter connection structure to each respective material of which catheters used at the medical facility might be manufactured.

The risk thus is present of an inappropriate match between a catheter and the catheter attachment structure by which it is to be coupled to a medical device. Therefore, consonant with the flexibility afforded by a large inventory of different catheter attachment structures and brands of medical devices, is the need to ensure that medical personnel are alert at all times to utilizing proper combinations of equipment. Correspondingly, there arises a need to train medical personnel in the appropriate procedures for each of the large number of different types of catheter attachment structures.

If an inappropriate catheter attachment structure is utilized, the attachment between a catheter and a medical device can leak, or even fail altogether.

Ensuring that a secure mechanical connection and a reliable fluid tight seal is effected between a catheter and a medical device is of utmost importance with regard to assemblies of a catheter and an attached medical device that is to be totally implanted within the body of a patient. In such a situation, an ineffective mechanical coupling or an improper fluid seal can result in major complications and expose a patient to painful, if not fatal, risks.

The failure of the mechanical coupling between an implanted catheter and an implanted medical device can result in one or the other becoming free to migrate throughout the body. Surgical intervention will then be required to locate and remove the loose article. Naturally under such conditions the delivery of medication or the withdrawal of fluid from any predetermined location in the body of the patient is totally frustrated.

Less dramatic, but possibly more insidious, is a catheter attachment with a medical device that is ineffective in producing a reliable fluid seal. Medication will then leak from the implanted assembly at the catheter attachment structure, diverting medication to an improper location. In many cases such misdelivered medication is damaging of tissue about the catheter attachment structure.

Such malfunctions may go undetected for some time, correspondingly resulting in the need for compensatory medical treatments to repair the damage produced. In addition, any failure to deliver medication in at a prescribed rate to a planned predetermined location will undermine the efficacy of a planned course of treatment. Naturally, if leaking is present in the system by which the medication is delivered, the time of the course of treatment will be extended.

Any of the circumstances described above will invariably require the removal of the catheter and the medical devices involved, the replacement of one or both, and then the surgical reimplantation of the entire assembly. Often this must occur at a fresh implantation site, as the original implantation and removal of such devices will have rendered the initial implantation site unusable, at least until a period of healing has passed.

All of these consequences of ineffective catheter attachment unnecessarily add to the duration and to the cost of medical procedures.

Even where an attachment is to be effected to the proximal end of a catheter outside the body of a patient, delay, equipment replacement, and enhanced costs can be anticipated, if a catheter attachment structure is used that is inappropriate to the material of which the associated catheter is made.

SUMMARY OF THE INVENTION

Accordingly, it is an object of the present invention to provide improved methods and systems for attaching catheters to medical devices.

It is another object of the present invention to provide methods and systems for attaching a selected catheter from a set of different kinds of catheters to a single medical device.

Yet another object of the present invention is to provide methods and apparatus for attaching either a silicone catheter or a polyurethane catheter to a single medical device.

Still another object of the present invention is to provide methods and apparatus that limit the number of attachment structures a hospital or other medical facility needs to purchase and store for attaching catheters to medical devices.

Another object of the present invention is to provide methods and apparatus that limit the number of medical devices used for attachment with a catheter that a medical facility needs to purchase and store.

It is also an object of the present invention to provide methods and apparatus for connecting opposing ends of a polyurethane catheter and silicone catheter together.

Also, another object of the present invention is to provide methods and apparatus for insuring a secure and liquid tight attachment between a catheter and a medical device.

Finally, it is another object of the present invention to provide methods and apparatus for limiting the number of different catheter attachment structures required in an operation using different kinds of catheters.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a catheter connection system is provided for effecting a fluid-tight coupling and a mechanical joinder between a medical device and a selected catheter chosen from either a silicone catheter or a polyurethane catheter. In some cases, the medical device accommodates a fluid flow. Such medical devices include access ports, leaflet ports, and catheter termination hubs. In the alternative, the medical device can be an instrument that does not accommodate fluid flow, such as a medical tunneling instrument.

The selected catheter to be attached to the medical device typically has a body wall with an exterior surface and with an interior surface that defines a longitudinally extending fluid flow lumen.

The catheter connection system includes a rigid, tubular stem having a proximal end attached in fluid communication to a medical device. The stem is further defined as having a free distal end opposite the proximal end and an exterior surface extending therebetween.

A plurality of comparably configured engagement barbs radially, outwardly extend on the exterior surface of the stem and encircle the stem. In one embodiment, three engagement barbs are present; one or two engagement barbs can be used in alternative embodiments. The engagement barbs have a maximum outer diameter so sized as to fit within the lumen of the selected catheter when the distal end of the stem is received within the lumen of the selected catheter.

A locking barb also radially, outwardly extends on the exterior surface of the stem and encircles the stem between the engagement barbs and the medical device. The locking barb has a maximum outer diameter that is larger than the maximum outer diameter of the engagement barbs.

The catheter connection system also includes a set of fastening assemblies. The set of fastening assemblies comprise a first fastening assembly corresponding to the silicone catheter and a second fastening assembly corresponding to the polyurethane catheter.

The first fastening assembly includes a first locking sleeve having a proximal end, a distal end, and an interior surface defining a passageway longitudinally extending therethrough. To attach the silicone catheter to the stem, the stem is received in the lumen of the silicone catheter, and the silicone catheter with the stem received therein is positioned within the passageway of the first locking sleeve. In this position, the interior surface of the first locking sleeve radially inwardly compresses a portion of the body wall of the silicone catheter against the locking barb on the stem.

The first fastening assembly also includes an annular compression ring extending inwardly from the interior surface of the first locking sleeve. The compression ring interacts with the locking barb to preclude unintentional disengagement of the silicone catheter from the stem.

The second fastening assembly comprises a second locking sleeve having a distal end, a proximal end, and an interior surface defining a passageway extending therebetween.

A pliable compression sleeve is longitudinally disposed within the passageway of the second locking sleeve. The compression sleeve has an interior surface defining a passageway longitudinally extending therethrough. To attach the polyurethane catheter to the stem, the stem is received in the lumen of the polyurethane catheter, and the polyurethane catheter with the stem received therein is positioned within the passageway of the compression sleeve. In this position, the interior surface of the compression sleeve radially inwardly compresses a portion of the body wall of the polyurethane catheter against the engagement barbs on the stem. Positioned at the proximal end of the locking sleeve is an opposing set of radially displacable resilient C-shaped clamps. The C-shaped clamps grasp the locking barb to prevent unintentional disengagement of the polyurethane catheter from the stem.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 6 is a cross-sectional view of the silicone catheter and the elements of the connection system of FIG. 5 shown in an assembled state thereof;

FIG. 7 is an exploded perspective view in partial breakaway of the elements of a fastening assembly for attaching the polyurethane catheter to the stem;

FIG. 8 is a cross-sectional view of part of the fastening assembly shown in FIG. 7;

FIG. 9 is a cross-sectional view of the stem in FIG. 3 being received within the lumen of the polyurethane catheter while the polyurethane catheter is disposed through a passageway in the fastening assembly shown in FIG. 7;

FIG. 10 is a cross-sectional view of the polyurethane catheter and the elements of the connection system of FIG. 7 shown in an assembled state thereof;

FIG. 15 is a plan view of a catheter repair or extension assembly for securing together opposing ends of different catheters using a catheter connection system embodying teaching of the present invention; and FIG. 16 is a plan view of a medical tunneling device having a stem extending therefrom for attachment to a selected catheter by a catheter connection system embodying teaching of the present invention.

DESCRIPTION OF THE PREFERRED EMBODIMENTS

Figure 1:
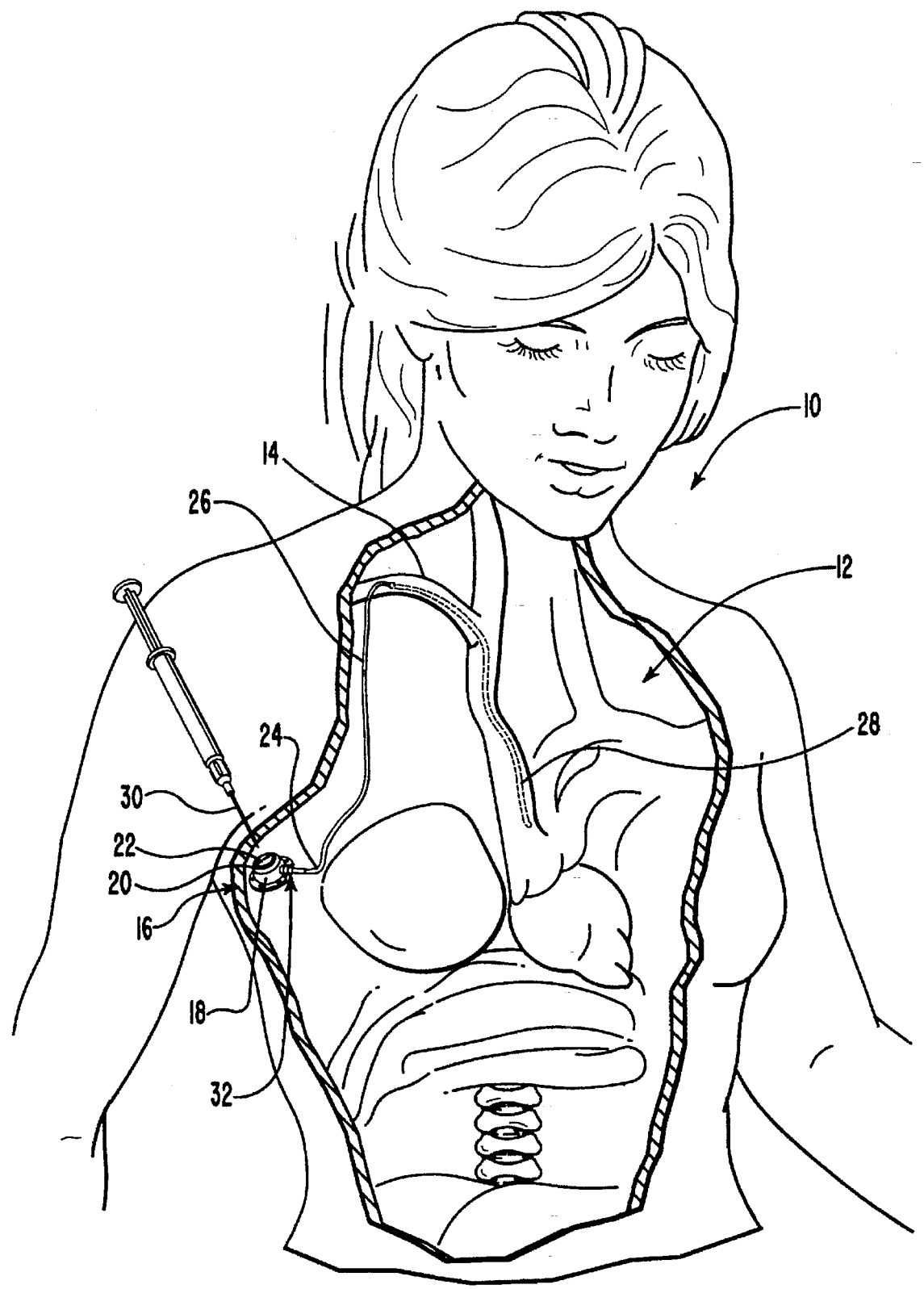
FIG. 1 is a perspective view of an access port implanted within a body of a patient and connected to a catheter by a catheter connection system embodying the teachings of the present invention.

Referring to FIG. 1, a patient 10 is shown having a chest 12 and a subclavian vein 14 therein. Implanted in chest 12 is an access port 16, which is one example of a medical device that can be used with the present invention. Access port 16 is shown as comprising a needle impenetrable housing 18 which encloses a fluid cavity, not shown in the figure, that is provided with an access opening 20. A needle penetrable septum 22 is retained in access opening 20 to seal the fluid cavity.

Also implanted in chest 12 is an elongated, pliable catheter 26 having a proximal end 24 attached in fluid communication to access port 16 by a catheter connection system 32. Catheter 26 is disposed in part within subclavian vein 14. A hypodermic needle 30 can penetrate septum 22 to deliver medication to the fluid cavity of access port 16. The medication then travels through catheter 26 and is discharged into the cardiovascular system of patient 10 at distal end 28 of catheter 26.

Figure 2:
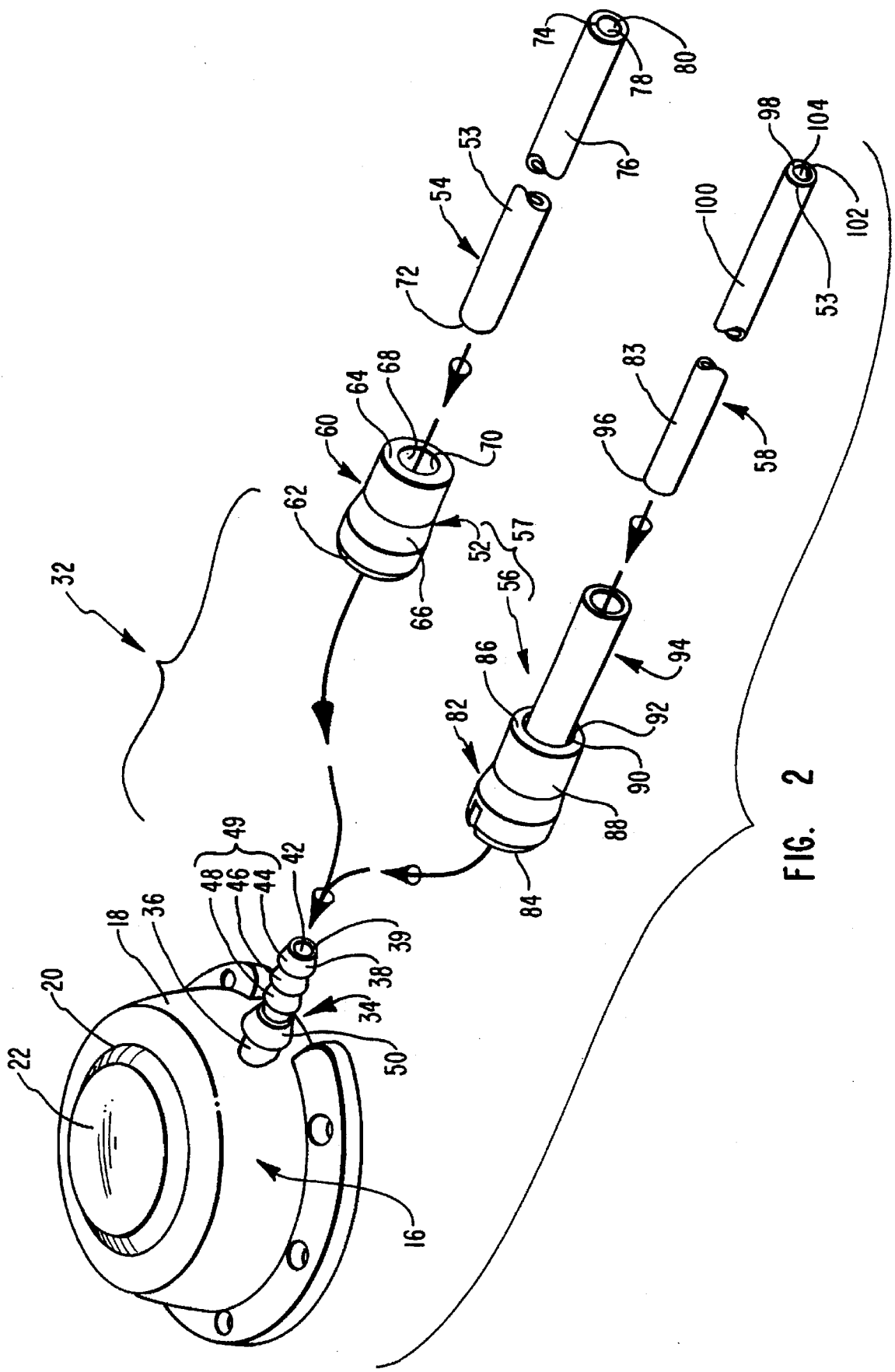
FIG. 2 is a perspective view of the access port of FIG. 1 with the catheter connection system thereof in disassembled condition, the catheter connection system including generally a stem extending from the access port and a set of fastening assemblies individually corresponding to either a silicone catheter or a polyurethane catheter.

FIG. 2 is an enlarged view of access port 16 with alternative elements of catheter connecting system 32 shown in a disassembled condition. FIG. 2 reveals catheter connection system 32 as comprising a rigid tubular stem 34 attached at proximal end 36 to access port 16 and having a free distal end 38 that tapers to a distal terminus 39. Extending between proximal end 36 and distal end 38 is an exterior surface 40 shown in FIG. 3 and discussed in detail subsequently relative thereto.

Stem 34 is depicted as being substantially cylindrical and having a passageway 42 longitudinally extending therethrough that is in fluid communication with access port 16. Stem 34 can have different cross-sectional configurations, such as elliptical, polygonal, or irregular configurations.

A first engagement barb 44 extends radially outwardly on exterior surface 40 at distal end 38 of stem 34 and encircles stem 34. A second engagement barb 46 and a third engagement barb 48 are consecutively aligned with first engagement barb 44 and likewise extends radially outwardly on exterior surface 40 of stem 34 and encircle stem 34. First engagement barb 44, second engagement barb 46, and third engagement barb 48 each have substantially the same configuration and are cumulatively referred to as engagement barbs 49.

A locking barb 50 extends radially, outwardly on exterior surface 40 of stem 34 and encircles stem 34 between third engagement barb 48 and proximal end 36 of stem 34. In one embodiment, stem 34 is made separately from access port 16 and is press fit thereinto. Stem 34 can thus be made from a different material than access port 16. Stem 34, engagement barbs 49, and locking barb 50 are substantially rigid elements which are preferably made from titanium. In the alternative, stem 34, engagement barbs 49, and locking barb 50 can be made from other metals, such as stainless steel, or from plastics, such as polycarbonate or acetal copolymer.

FIG. 2 further reveals catheter connection system 32 as comprising a first fastening assembly 52 that includes a rigid first locking sleeve 60. First locking sleeve 60 is shown as having a proximal end 62, a distal end 64, and an exterior surface 66 extending therebetween. Furthermore, first locking sleeve 60 has an interior surface 68 defining a passageway 70 longitudinally extending therethrough. First locking sleeve 60 is preferably molded formed from polycarbonate. In the alternative, first locking sleeve 60 can be made from other plastics, such as acetal copolymer, or from a metal, such as titanium or stainless steel.

Operative with first fastening assembly 52 is an elongated, pliable silicone catheter 54 having a body wall 53 with an exterior surface 76 extending between a proximal end 72 and a distal end 74. Body wall 53 of silicone catheter 54 also has an interior surface 78 that defines a lumen 80 longitudinally extending through catheter 54.

In the alternative to using first fastening assembly 52, catheter connection system 32 also includes a second fastening assembly 56. First fastening assembly 52 and second fastening assembly 56 comprise a set of fastening assemblies 57. Second fastening assembly 56 is shown in FIG. 2 as comprising a rigid second locking sleeve 82 having a proximal end 84, a distal end 86, and an exterior surface 88 extending therebetween. Longitudinally extending through second locking sleeve 82 is a passageway 90 defined by an interior surface 92. Disposed within passageway 90 is an elongated compression sleeve 94 which will be discussed later. As second locking sleeve 82 includes more intricately shaped components than first locking sleeve 60, Second locking sleeve 82 is preferably machined from acetal copolymer. In the alternative, second locking sleeve 82 can be fashioned from other plastic such as polycarbonate or from metals, such as titanium or stainless steel.

Operative with second fastening assembly 56 is an elongated polyurethane catheter 58 that is less pliant than silicone catheter 54. Polyurethane catheter 58 has a body wall 83 with an exterior surface 100 extending between a proximal end 96 and a distal end 98. Body wall 83 of polyurethane catheter 58 has an interior surface 102 defining a lumen 104 longitudinally extending therethrough.

Figure 3:
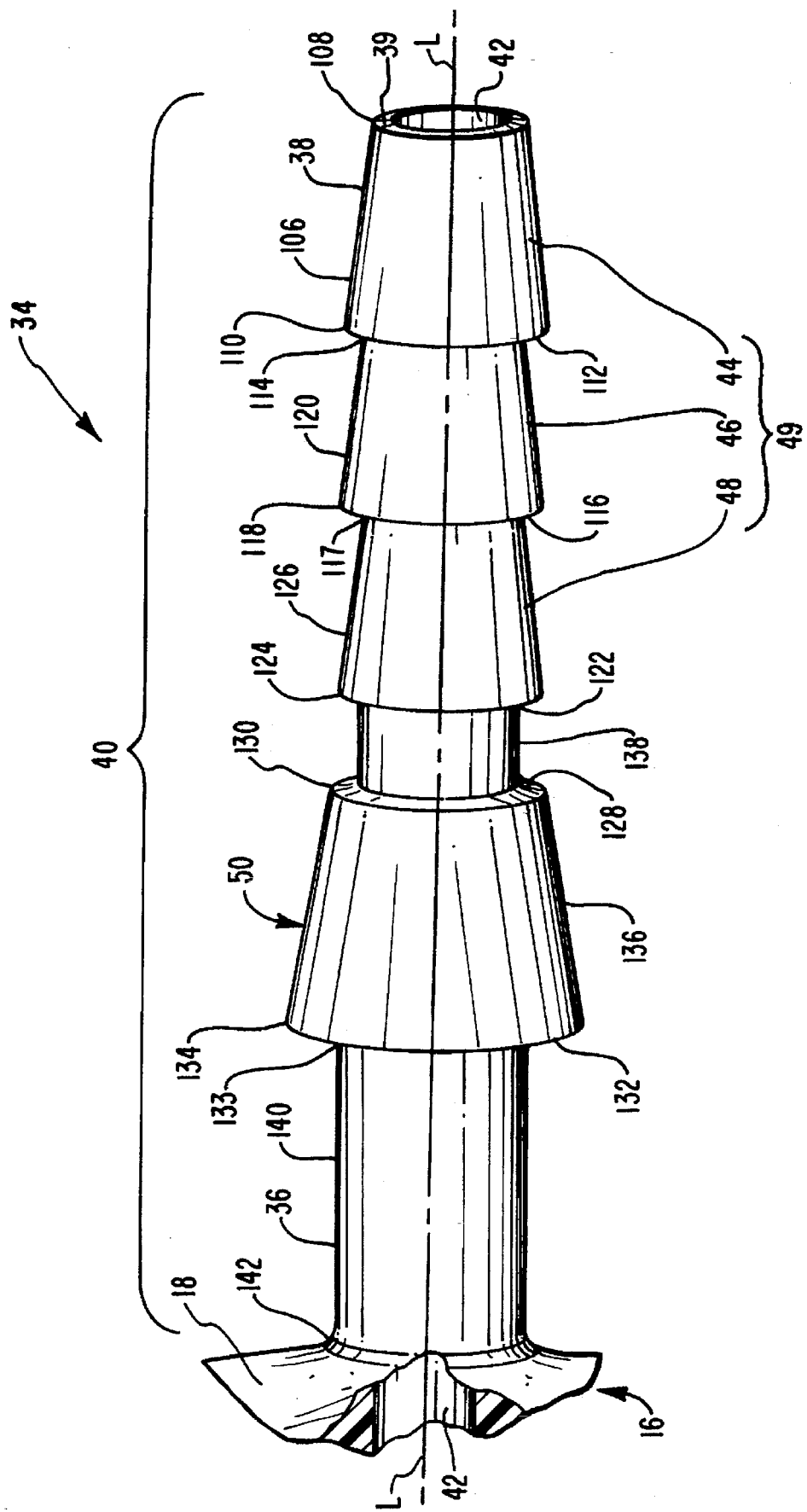
FIG. 3 is an enlarged side view of the stem in FIG. 2.

FIG. 3 is an enlarged side view of stem 34. First engagement barb 44 is depicted therein as terminating at one end thereof in a distal tip 108 that encircles stem 34 at distal terminus 39 thereof annular first barb face 112 encircles stem 34 and extends radially outward therefrom along a plane perpendicular to the longitudinal axis L of stem 34 to an outer ridge 110 at the opposite end of first engagement barb 44. A frustoconical first engagement surface 106 encircles stem 34 and extends increasingly radially outwardly therefrom in a direction from distal tip 108 to outer ridge 110.

In a similar fashion, second engagement barb 46 comprises a distal tip 114 that encircles stem 34 adjacent to first barb face 112. An annular second barb face 116 encircles stem 34 and extends radially outward therefrom along a plane perpendicular to the longitudinal access of stem 34 to an outer ridge 118. A frustoconical second engagement surface 120 encircles stem 34 and extends increasingly radially outwardly therefrom in a direction from distal tip 114 to outer ridge 118.

In like manner, third engagement barb 48 comprises a distal tip 117 that encircles stem 34 adjacent to second barb face 116. An annular third barb face 122 encircles stem 34 and extends radially outward therefrom along a plane perpendicular to the longitudinal axis L of stem 34 to an outer ridge 124 of third engagement barb 48. A frustoconical third engagement surface 126 encircles stem 34 and extends increasingly radially outwardly therefrom in a direction from distal tip 117 to outer ridge 124.

Locking barb 50 is depicted in FIG. 3 as comprising an annular distal side wall 128 that encircles stem 34 and extends radially outwardly therefrom along a plane perpendicular to the longitudinal axis L of stem 34 to an outside corner 130. Locking barb 50 also comprises an annular proximal side wall 132 that encircles stem 34 and extends radially outwardly therefrom in a direction from an inside corner 133 on stem 34 to an outside corner 134 of locking barb 50 that is distal of inside corner 133. Outside corner 134 has an outer diameter that is larger than the outer diameter of outside corner 130.

Figure 4:
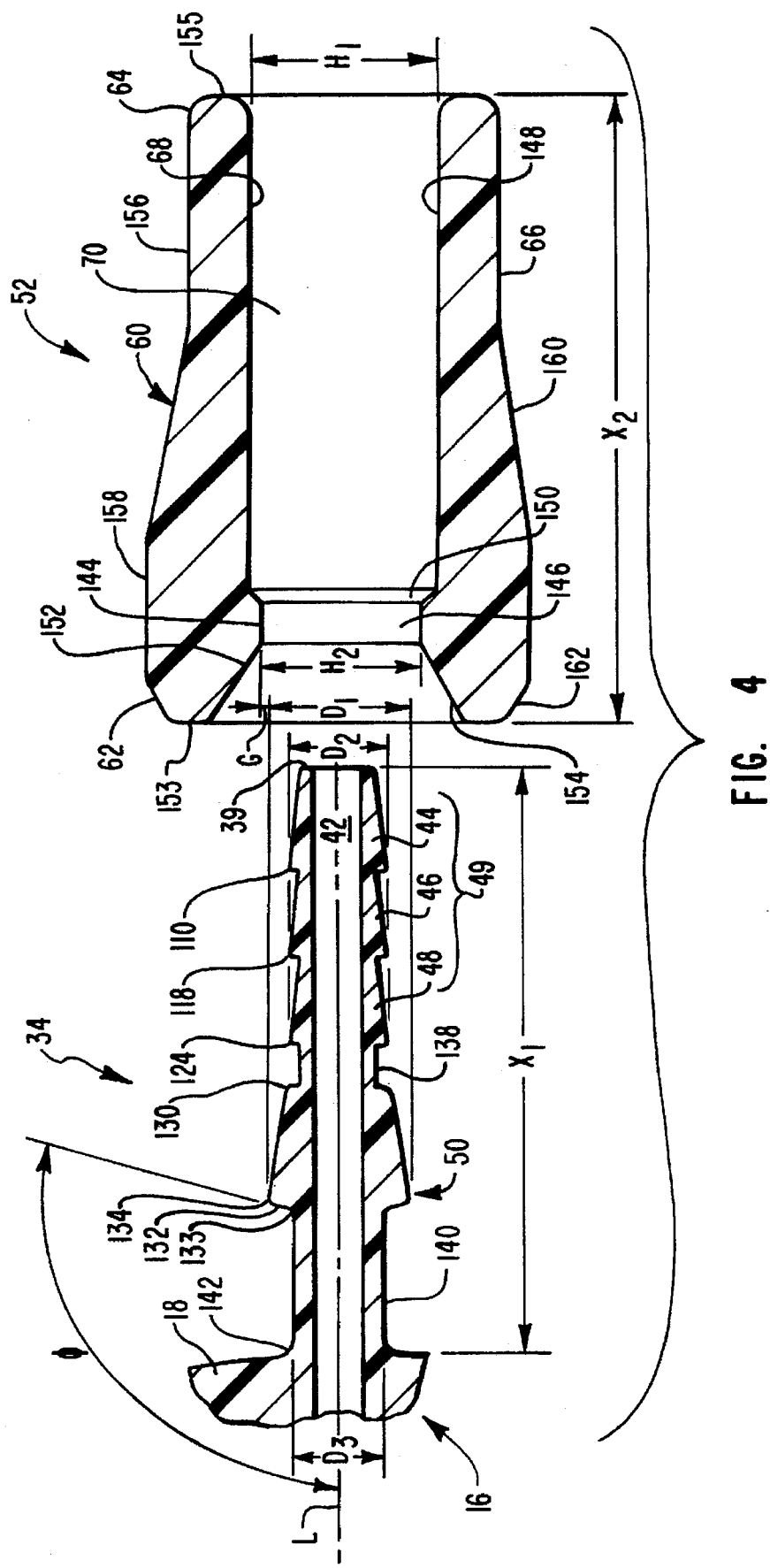
FIG. 4 is a cross-sectional view of the stem shown in FIG. 3 and the particular fastening assembly used for attaching the silicone catheter to the stem.

Proximal side wall 132 extends between inside corner 133 and outside corner 134 at an angle $\phi$ shown in FIG. 4 to be greater than 90°. Angle $\phi$ is measured between proximal side wall 132 and the longitudinal axis L of stem 34 proximal of proximal side wall 132. Preferably angle $\phi$ is in a range from about 95° to about 125°. Locking barb 50 also includes a frustoconical surface 136 that encircles stem 34 and extends increasingly radially outwardly therefrom in a direction from outside corner 130 of distal side wall 128 to outside corner 134 of proximal side wall 132. Surface 136 and proximal side wall 132 are shown in FIG. 4 at a right angle to each other.

Extending between distal side wall 128 of locking barb 50 and third barb face 122 of third engagement barb 48 is a first cylindrical portion 138 of stem 34. Extending between proximal side wall 132 of locking barb 50 and access port 16 is a second cylindrical portion 140 of stem 34. Stem 34 is attached to access port 16 at an extreme proximal end 142 of stem 34.

A cross-sectional view of stem 34 in FIG. 4 discloses outside corner 134 of locking barb 50 as having an outer diameter $D_1$. Outer ridges 110, 118, and 124 of engagement barbs 49, as shown in FIG. 3, each have the same outer diameter $D_2$, which is smaller than outer diameter $D_1$ of locking barb 50. Stem 34 has a length $X_1$ from extreme proximal end 142 to distal terminus 39, and, second cylindrical portion 140 has an outer diameter $D_3$.

Also depicted in FIG. 4 is a cross-sectional view of first fastening assembly 52 showing first locking sleeve 60 as including an annular proximal end face 153, an opposing annular distal end face 155, and a length $X_2$ therebetween. Interior surface 68 of first locking sleeve 60 is shown as including a radially inwardly extending annular compression ring 144, and having a substantially cylindrical portion 148 extending between compression ring 144 and distal end face 155. Cylindrical portion 148 is shown as having an inner diameter $H_1$.

Compression ring 144 comprises a cylindrical compression surface 146 and a distal shoulder 150 that slopes radially outward to cylindrical portion 148. Compression surface 146 of compression ring 144 has an inner diameter $H_2$ that is smaller than inner diameter $H_1$ of cylindrical portion 148. Inner diameter $H_2$ of compression surface 146 is slightly larger outer diameter $D_1$ of locking barb 50, so that an annular gap cap G results between compression surface 146 and outside corner 134 of locking barb 50.

Compression ring 144 is also partially defined by a proximal shoulder 152 that slopes radially outward from compression surface 146 to proximal end face 153 of first locking sleeve 60, thereby forming an enlarged receiving mouth 154.

Exterior surface 66 of first locking sleeve 60 includes first cylindrical surface 156 positioned at distal end 64 of first locking sleeve 60 and a second cylindrical surface 158 positioned at proximal end 62 of first locking sleeve 60. Second cylindrical surface 158 has a larger outer diameter than first cylindrical surface 156. A sloped transition shoulder 160 extends between first cylindrical surface 156 and second cylindrical surface 158.

Transition, and shoulder 160 better enables a user to grasp and position first fastening assembly 52 in the manner to be discussed later. In alternative embodiments, exterior surface 66 of first locking sleeve 60 can be ribbed, cylindrical, textured, or of any other configuration that could be of assistance in the manipulation of first fastening assembly 52. To eliminate sharp edges, a corner shoulder 162 extends between second cylindrical surface 158 and proximal end face 153 on first locking sleeve 60.

Figure 5:
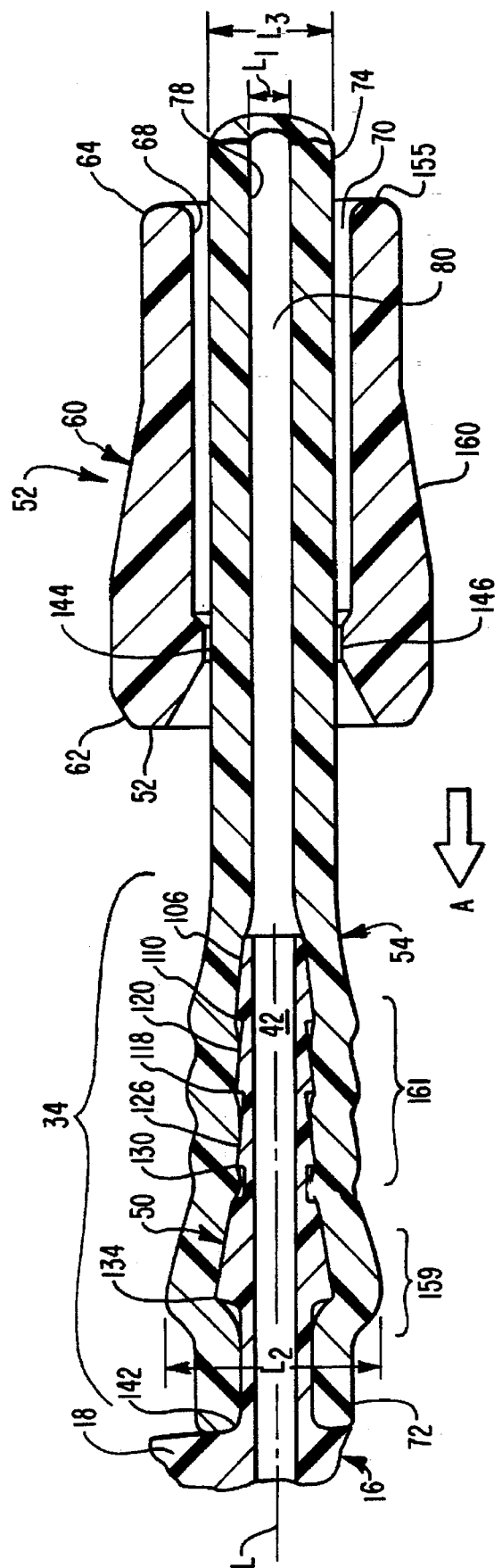
FIG. 5 is a cross-sectional view of the stem in FIG. 4 being received within the lumen of the silicone catheter while the silicone catheter is disposed through a passageway in the fastening assembly.

As depicted in FIG. 5, to attach silicone catheter 54 to access port 16, stem 34 is initially received within lumen 80 of silicone catheter 54 by sliding silicone catheter 54 over engagement barbs 49 and locking barb 50 until proximal end 72 of silicone catheter 54 abuts against housing 18 of access port 16. Lumen 80 of silicone catheter 54 is shown as having an inner diameter $L_1$ that is smaller than outer diameter D shown in FIG. 4 of outside corner 134 of locking barb 50. Accordingly, once stem 34 is received within lumen 80, a first expansion portion 159 of silicone catheter 54 over locking barb 50 is urged radially outward. First expansion portion 159 has a an outer diameter $L_2$. The normal or unexpanded remaining portion of silicone catheter 54 has an outer diameter $L_3$.

In the embodiment shown in FIG. 5, outer diameter $D_2$ of engagement barbs 49 is larger than inner diameter $L_1$ of lumen 80 of silicone catheter 54. As a result, a second expansion portion 161 of silicone catheter 54 over engagement barbs 49 is urged radially outwardly. Outer diameter $D_2$ of engagement barbs 49 may alternatively be smaller than inner diameter $L_1$ of lumen 80 of silicone catheter 54.

Also depicted in FIG. 5 is a cross-sectional view of first fastening assembly 52 with silicone catheter 54 passing through passageway 70 thereof. By advancing first fastening assembly 52 in the direction of arrow A shown in FIG. 5, stem 34 within lumen 80 of silicone catheter 54 is eventually received within passageway 70 of first locking sleeve 60 as shown in FIG. 6. First fastening assembly 52 is advanced in the direction of arrow A until compression ring 144 passes over locking barb 50 and is positioned between locking barb 50 and access port 16.

Although inner diameter $H_2$ of compression ring 144 and inner diameter $H_1$ of cylindrical portion 148 are each larger than outer diameter $D_1$ of locking barb 50, inner diameter $H_2$ and inner diameter $H_1$ are each smaller than outer diameter $L_2$ of first expansion portion 159 of silicone catheter 54 over locking barb 50. Accordingly, as compression ring 144 passes over locking barb 50, first expansion portion 159 of silicone catheter 54 is compressed therebetween. Annular gap G shown in FIG. 4 between locking barb 50 and compression ring 144 is sufficiently large, however, so that first expansion portion 159 is not ruptured or sheared in the process. Once compression ring 144 passes to the proximal side of locking barb 50, first expansion portion 159 again expands, but still remains compressed between cylindrical portion 148 of first locking sleeve 60 and locking barb 50.

Accordingly, with first fastening assembly 52 positioned as shown in FIG. 6, compression ring 144 and interior surface 68 of first locking sleeve 60 radially, inwardly compresses body wall 83 of silicone catheter 54 against locking barb 50 and stem 34 to create a fluid-tight coupling between stem 34 and silicone catheter 54. The interaction between compression ring 144, silicone catheter 54, and locking barb 50 also creates a mechanical joinder therebetween which precludes unintentional disengagement of silicone catheter 54 from stem 34.

In the embodiment shown in FIG. 6, interior surface 68 of first locking sleeve 60 also compresses second expansion portion 161 of body wall 83 against engagement barbs 49. Although unnecessary, this interaction between engagement barbs 49 and body wall 83 assists in the formation of the liquid-tight seal and the mechanical joinder between stem 34 and silicone catheter 54.

Referring now to FIG. 7, second fastening assembly 56 is seen to comprise a second locking sleeve 82 and a compression sleeve 94. Compression sleeve 94 comprises a body wall 170 having a proximal end 164, a distal end 166, and an exterior surface 168 extending therebetween. A passageway 171 longitudinally extends through compression sleeve 94 and is defined by an interior surface 173. Passageway 171 has an inner diameter M.

Compression sleeve 94 further comprises a substantially cylindrical head portion 172 having an annular proximal end face 174 and an annular distal end face 176. Axially aligned with and extending from distal end face 176 is a tail portion 178 which terminates at a distal end face 180. Tail portion 178 has an outer diameter that is smaller than the outer diameter of head portion 172. Compression sleeve 94 is preferably made from silicone, although other pliant compressible materials can be used.

Also depicted in FIG. 7 is second locking sleeve 82 which includes a pair of opposing, resilient C-shaped clamps 182 and 184 positioned at proximal end 84 thereof. C-shaped clamps 182 and 184 are separated by a first slot 186 and a second slot 188 which extend through proximal end 84 of second locking sleeve 82 along an axis perpendicular to the longitudinal axis of second locking sleeve 82. First slot 186 and a second slot 188 enable C-shaped clamps 182 and 184 to pivot away from each other, expanding first slot 186 and second slot 188 therebetween, when an outwardly directed radial force is imposed on either of C-shaped clamps 182, 184. In alternative embodiments, a single slot or more than a pair of slots can extend through proximal end 84 of second locking sleeve 82 to form a corresponding number of resilient clamps.

Second locking sleeve 82 is depicted in a cross-sectional view in FIG. 8. As shown therein, second locking sleeve 82 has a proximal end face 212, an annular distal end face 216, and a length $X_3$ therebetween. Distal end face 216 in part defines an annular bracing ring 190 that extends radially inwardly from interior surface 92 at distal end 86 of second locking sleeve 82. Bracing ring 190 is defined by an annular proximal side wall 218 and an interior surface 220 that extends between proximal side wall 218 and distal end face 216 of second locking sleeve 82.

Extending between C-shaped clamp 182 and bracing ring 190 on interior surface 92 is a cylindrical compression portion 192. C-shaped clamps 182 and 184 together comprise an arm 194 extending longitudinally from compression portion 192. An attachment ridge 196 projects radially inwardly from arm 194 and terminates at an interior surface 202 with an inner diameter N. Attachment ridge 196 includes sloping proximal shoulder 198 that extends outward from interior surface 202 to proximal end face 212 of second locking sleeve 82. An annular distal end face 200 extends from interior surface 202 to arm 194.

Exterior surface 88 of second locking sleeve 82 has a first cylindrical surface 204 positioned at distal end 86 and a second cylindrical surface 206 positioned at proximal end 84. Second cylindrical surface 206 has a larger outer diameter than close first cylindrical surface 156. A sloped transition shoulder 208 extends between first cylindrical surface 204 and second cylindrical surface 206. Transition shoulder 208 serves the same purpose as discussed with regard to transition shoulder 160 of first locking sleeve 60. Likewise exterior surface 88 can have the same alternative embodiments as exterior surface 66 of first locking sleeve 60. To eliminate sharp edges, a corner shoulder 210 extends between second cylindrical surface 206 and proximal end face 212 on second locking sleeve 82.

Depicted in FIG. 9, head portion 172 of compression sleeve 94 is disposed within second locking sleeve 82. Exterior surface 168 of head portion 172 is biased against compression portion 192 of second locking sleeve 82; proximal end face 174 of head portion 172 is biased against distal end face 200 of attachment ridge 196; and distal end face 176 of head portion 172 is biased against proximal side wall 218 of bracing ring 190. Compression sleeve 94 can be disposed in locking sleeve 82, or can be secured to second locking sleeve 82 by an adhesive.

To attach polyurethane catheter 58 to access port 16, stem 34 is initially received within lumen 104 of polyurethane catheter 58 by sliding polyurethane catheter 58 over engagement barbs 49 until proximal end 96 of polyurethane catheter 58 abuts distal side wall 128 of locking barb 50. Lumen 104 of polyurethane catheter 58 has an inner diameter $Y_1$ that is slightly smaller than maximum outer diameter $D_2$ of engagement barbs 49. Accordingly, as stem 34 is received within lumen 104 an expansion portion 220 of polyurethane catheter 58 over engagement barbs 49 is urged radially outwardly. Expansion portion 220 has a maximum outer diameter $Y_2$. The normal or unexpanded remaining portion of polyurethane catheter 58 has an outside diameter $Y_3$.

Polyurethane catheter 58 is also shown in FIG. 9 extending through passageway 171 of compression sleeve 94. By urging second fastening assembly 56 in the direction of arrow B shown in FIG. 9, stem 34 within lumen 104 of polyurethane catheter 58 is received within passageway 171 of compression sleeve 94 as shown in FIG. 10.

Inner diameter N of attachment ridge 196 is smaller than maximum outer diameter $D_1$ of locking barb 50. Accordingly, as second fastening assembly 56 is advanced in the direction of arrow B, attachment ridge 196 passes over engagement barbs 49 and is urged against radially expanding, frustoconical top surface 136 of locking barb 50.

The force applied to second fastening assembly 56 in the direction of Arrow B causes C-shaped clamps 182 and 184 to radially expand and pass over outer corner 134 of locking barb 50. The resilience of C-shaped clamps 182 and 184 then causes C-shaped clamps 182 and 184 to spring closed, such that attachment ridge 196 becomes biased against proximal side wall 132 of locking barb 50. The interaction between C-shaped clamps 182 and 184 and locking barb 50 creates a mechanical joinder that precludes unintentional disengagement of stem 34 from polyurethane catheter 58.

The springing or constricting force of C-shaped clamps 182 and 184 works in conjunction with the slope of proximal side wall 132 to cause second fastening assembly 56 to be continually urged in the direction of arrow B. The slope of proximal side wall 132 does, however, permit the removal of second fastening assembly 56 by applying a force to second fastening assembly 56 in the direction opposite of arrow B.

Maximum outer diameter $Y_2$ of expansion portion 220 is larger than inner diameter M of passageway 171 of compression sleeve 94. Accordingly, with C-shaped clamps 182 and 184 positioned as discussed above, interior surface 92 of second fastening assembly 56 and head portion 172 of compression sleeve 94 radially, inwardly compresses expansion portion 220 of polyurethane catheter 58 against engagement barbs 49 and stem 34 to create a fluid tight coupling between stem 34 and polyurethane catheter 58.

Figure 11:
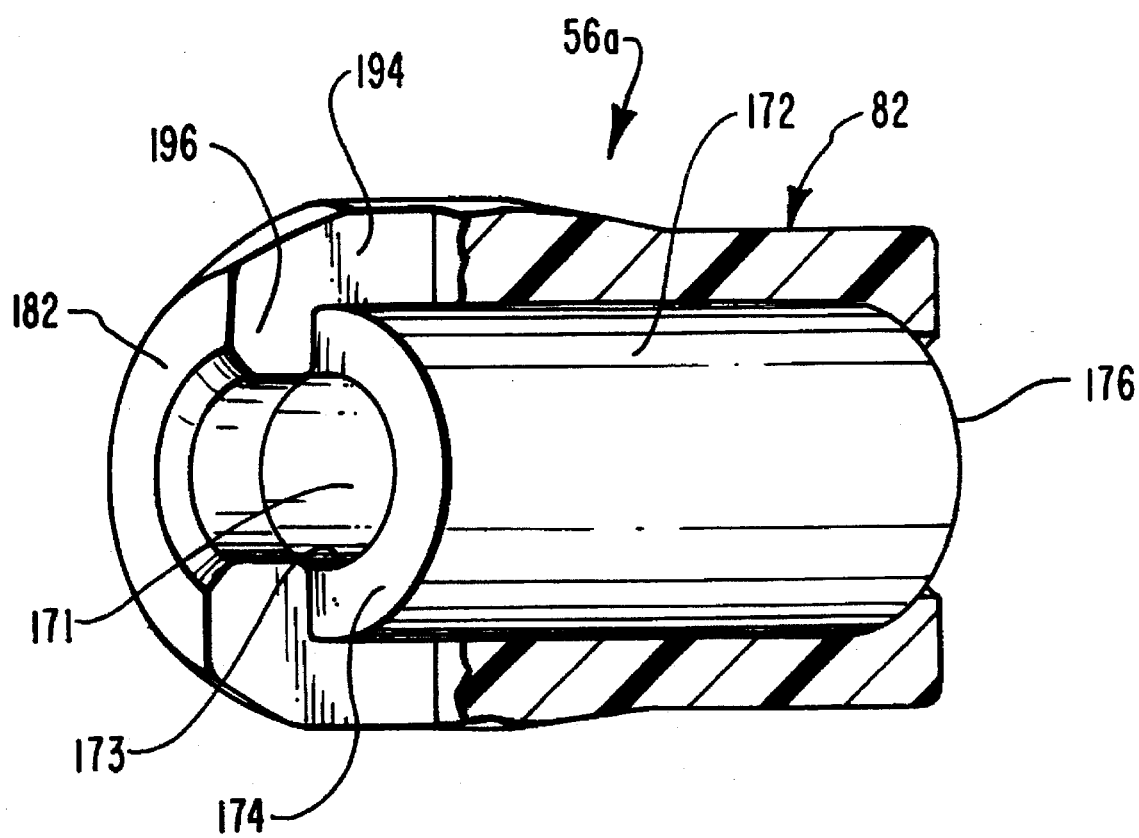
FIG. 11 is a perspective view in partial breakaway of a second embodiment of a fastening assembly for attaching the polyurethane catheter to the stem.

As shown in FIG. 10, a distal portion 214 of compression sleeve 94 encircle and supports polyurethane catheter 58 distal of distal end 86 of second locking sleeve 82 to prevent sharp bending in polyurethane catheter 58 which could result in kinking or pinching of polyurethane catheter 58 at that location. In an alternative embodiment of a second fastening assembly 56a shown in FIG. 11, tail portion 178 of compression sleeve 94 is eliminated, and only head portion 172 is used with second locking sleeve 82.

The embodiment of catheter connection system 32 disclosed above is used with silicone catheter 54 and polyurethane catheter 58. In the alternative, catheter connection system 32 can be used with any first and second catheter where, the first and second catheter are made from different materials, and one material is less pliant than the other material. The catheter made of the less pliant material is then secured to stem 34 by second fastening assembly 56, and the catheter made of the other material is secured to stem 34 by first fastening assembly 52.

The size and dimensions of engagement barbs 49, locking barb 50, first fastening assembly 52, and second fastening assembly 56 depend on the size of the inner and outer diameter of the corresponding catheters used and on the materials from which the corresponding catheters are made. For example, the outer diameters of locking barb 50 and engagement barbs 49 generally increase as the inner diameter of the catheter corresponding to each of these attachment structures increases.

As compliance decreases in the material from which a catheter is made, the difference generally decreases between the inside diameter of the catheter and the maximum outer diameter of the corresponding attachment structures, such as locking barb 50 or engagement barbs 49.

Since the size of locking barb 50 and engagement barbs 49 vary depending on the specific catheter to be attached thereto, the size of locking barb 50 and engagement barbs 49 can vary independent of each other. For example, to selectively attach either a silicone catheter having a relatively small inner diameter or a polyurethane catheter having a relatively large inner diameter to stem 34, it may be necessary to decrease the outer diameter of locking barb 50 and increase the outer diameter of engagement barbs 49.

Outlined below are selected dimensions for one embodiment of a catheter connection system, such as catheter connection system 32 disclosed above, for use alternatively with a selected one of a polyurethane catheter, such as polyurethane catheter 58, and a silicone catheter, such as silicone catheter 54. Thus, selected dimensions for these specific catheters are also provided. In each case the dimensions are identified by corresponding reference characters shown in selected of the figures already discussed above. All dimensions are given in inches.

Silicone catheter 54 has the following dimension as shown in FIG. 5:

$L_1$=0.02–0.04

$L_3$=0.08–0.01

Polyurethane catheter 58 has the following dimensions as shown in FIG. 9:

$Y_1$=0.03–0.05

$Y_3$=0.05–0.07

Stem 34, locking barb 50, and engagement barbs 49 are made of titanium and have the following dimensions as shown in FIG. 4:

$X_1$=0.34–0.36

$D_1$=0.08–0.10

$D_2$=0.04–0.06

$D_3$=0.04–0.06

First fastening assembly 52 is made of polycarbonate and has the following dimensions as shown in FIG. 4:

$X_2$=0.35–0.37

$H_1$=0.17–0.19

$H_2$=0.09–0.11

Finally, second fastening assembly 56 includes second locking sleeve 82 made of acetal copolymer and compression sleeve 94 made of silicone. Second fastening assembly 56 has the following dimensions as shown in FIGS. 7 and 8:

$X_3$=0.31–0.33

N=0.08–0.09

M=0.06–0.08

In accordance with one aspect of the present invention, a catheter connection system, such as catheter connection system 34, is provided with attachment means on exterior surface 40 of stem 34 for engaging the interior surface of a selected catheter chosen from either a first catheter of a first material or a second catheter of a second material, where the second material is less pliant than the first material. The interior surface of the selected catheter is engaged when distal end 38 of stem 34 is received in the lumen of the selected catheter. The attachment means also enables locking of the selected catheter on stem 34.

By way of example and not by limitation, one form of the structures capable of performing the function of such an attaching means and disclosed herein includes engagement barbs 49 and locking barb 50 that are on exterior surface of stem 34. As shown and discussed with regard to FIGS. 5 and 6 above, locking barb 50 engages interior surface 78 of silicone catheter 54 when stem 34 and locking barb 50 are received in lumen 80 of silicone catheter 54. Likewise, as shown and discussed with regard to FIGS. 9 and 10 above, engagement barbs 49 engage interior surface 102 of polyurethane catheter 58 when stem 34 and engagement barbs 49 are received in lumen 104 of polyurethane catheter 58.

As discussed with regard to FIG. 6, locking barb 50 enables the locking of silicone catheter 54 onto stem 34 by the interaction of locking barb 50 with compression ring 144 through silicone catheter 54. Similarly, as discussed with regard to FIG. 10, locking barb 50 enables the locking of polyurethane catheter 58 onto stem 34 by the interaction of locking barb 50 directly with attachment ridge 196 of second fastening assembly 56.

Alternative configurations of structures performing the functions of such an attachment means are possible. Such attachment structures could include, but would not be limited to, the use of a single engagement barb, two engagement barbs, or any plurality of engagement barbs. Furthermore, the locking barb and engagement barbs could be of different sizes and configurations from those already disclosed. Some of these embodiments will be shown in later figures.

In accordance with yet another aspect of the present invention there is also provided securing means that is operative when distal end 38 of stem 34 is received in the lumen of the selected catheter for performing two distinct functions. The first function is to radially, inwardly compress a portion of a body wall of the selected catheter against a portion of exterior surface 40 of stem 34. The second function of the securing means is to interact with structures performing the function of the attachment means as discussed above to preclude unintentional disengagement of the selected catheter from stem 34.

By way of example and not limitation, one form of structure capable of performing the function of such a securing means and disclosed herein includes first fastening assembly 52, as depicted in FIGS. 2–6, and second fastening assembly 56, as depicted in FIGS. 7–10.

As discussed above in greater detail, when first fastening assembly 52 is positioned as shown in FIG. 6, interior surface 68 of first locking sleeve 60 radially, inwardly compresses expansion portion 159 of silicone catheter 54 against locking barb 50 on stem 34. Interior surface 68 of first locking sleeve 60 may compress a portion of silicone catheter 54 against engagement barbs 49, but this is incidental and unnecessary for proper attachment of silicone catheter 54 to stem 34.

In like manner, when second fastening assembly 56 is positioned as shown in FIG. 10, interior surface 173 of compression sleeve 94 radially, inwardly compresses expansion portion 220 of polyurethane catheter 58 against engagement barbs 49 on stem 34.

As discussed with regard to FIGS. 6, compression ring 144 of first fastening assembly 52 interacts indirectly with locking barb 50 through silicone catheter 54 to preclude unintentional disengagement of silicone catheter 54 from stem 34. The interaction between first fastening assembly 52 and locking barb 50 is considered to be "indirect", since first fastening assembly 52 and locking barb 50 do not directly contact each other, but instead interact through silicone catheter 54. As discussed with regard to FIG. 10, attachment ridge 196 of second fastening assembly 56 interacts directly with locking barb 50 to preclude unintentional disengagement of 24 polyurethane catheter 58 from stem 34.

Figure 12:
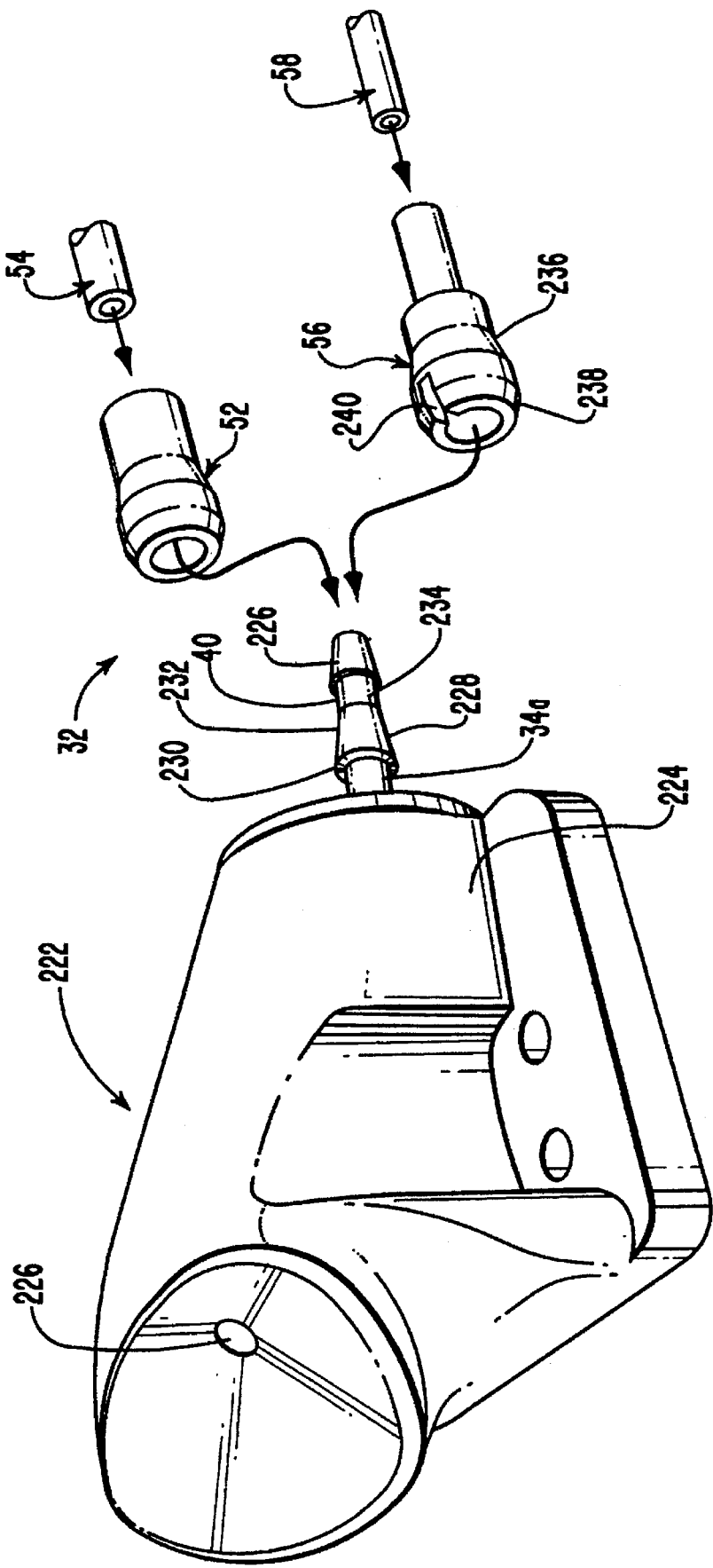
FIG. 12 is a perspective view of a second embodiment of a stem extending from a leaflet port for attachment to a catheter by use of a catheter connection system embodying teaching of the present invention.

The term "medical device" as used in the specification and appended claims is intended to include any tool, instrument, apparatus or device to which it is desirable to attach a catheter in either fluid flow communication or otherwise. The above discussed embodiment of a catheter connection system 32 has been disclosed in the context of attaching a selected catheter in fluid communication to access port 16. An alternative example of a medical device that can be used with an embodiment of catheter connection system 32 is a leaflet port 222, depicted in FIG. 12.

Leaflet port 222 is shown having a housing 224 with an access channel 225 leading to a leaflet valve not shown but enclosed within housing 224. Extending from housing 224 is a stem 34a. In this embodiment of catheter connection system 32, a single engagement barb 226 is positioned on stem 34a as opposed to a plurality of engagement barbs, such as engagement barbs 49.

A locking barb 228 is positioned stem 34a between single engagement barb 226 and leaflet port 222. Locking barb 228 is distinguished from locking barb 50 in that distal sidewall 128 of locking barb 50 has been eliminated from locking barb 228. Accordingly, locking barb 228 comprises a proximal sidewall 230 that is comparable to proximal sidewall 132 of locking barb 50 and a frustoconical top surface 232 that extends directly from proximal sidewall 230 to exterior cylindrical area 234 of stem 34a.

First fastening assembly 52 is shown for attaching silicone catheter 54 to stem 34a. Second fastening assembly 56 is shown for attaching polyurethane catheter 58 to stem 34a. In an alternative embodiment of catheter connection system 32, second locking sleeve 236 has a proximal end 238 with only a single slot 240 extending therethrough.

Figure 13:
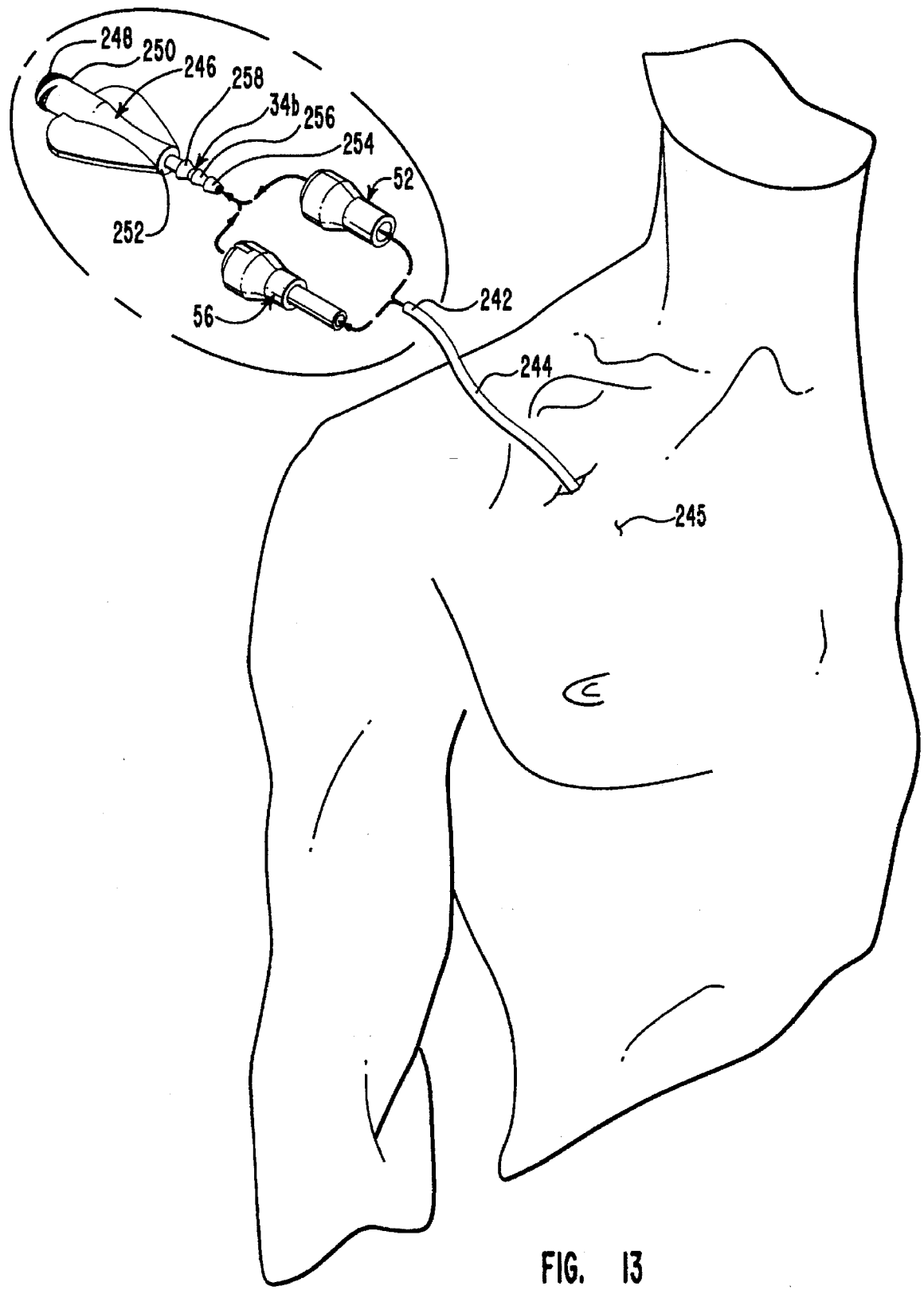
FIG. 13 is a perspective view of a proximal end of a catheter extending from a body of a patient for connection by one of a set of fastening assemblies to a catheter termination hub.

As shown in FIG. 13, another example of a medical device that accommodates a fluid flow and can be used with catheter connection system 32 is a catheter termination hub 246. Catheter termination hub 246 has a proximal end 248 to threads 250 positioned thereat for connection with an medical device not shown and includes a distal end 252 with a stem 34b extending therefrom. In the embodiment disclosed, stem 34b includes only a first engagement barb 254, a second engagement 256, and a locking barb 258. FIG. 13 also depicts a proximal end 242 of a catheter 244 extending from chest 245 of a patient for attachment to stem 34b by either first fastening assembly 52 or second fastening assembly 56, depending on the material composition of catheter 244.

Figure 14:
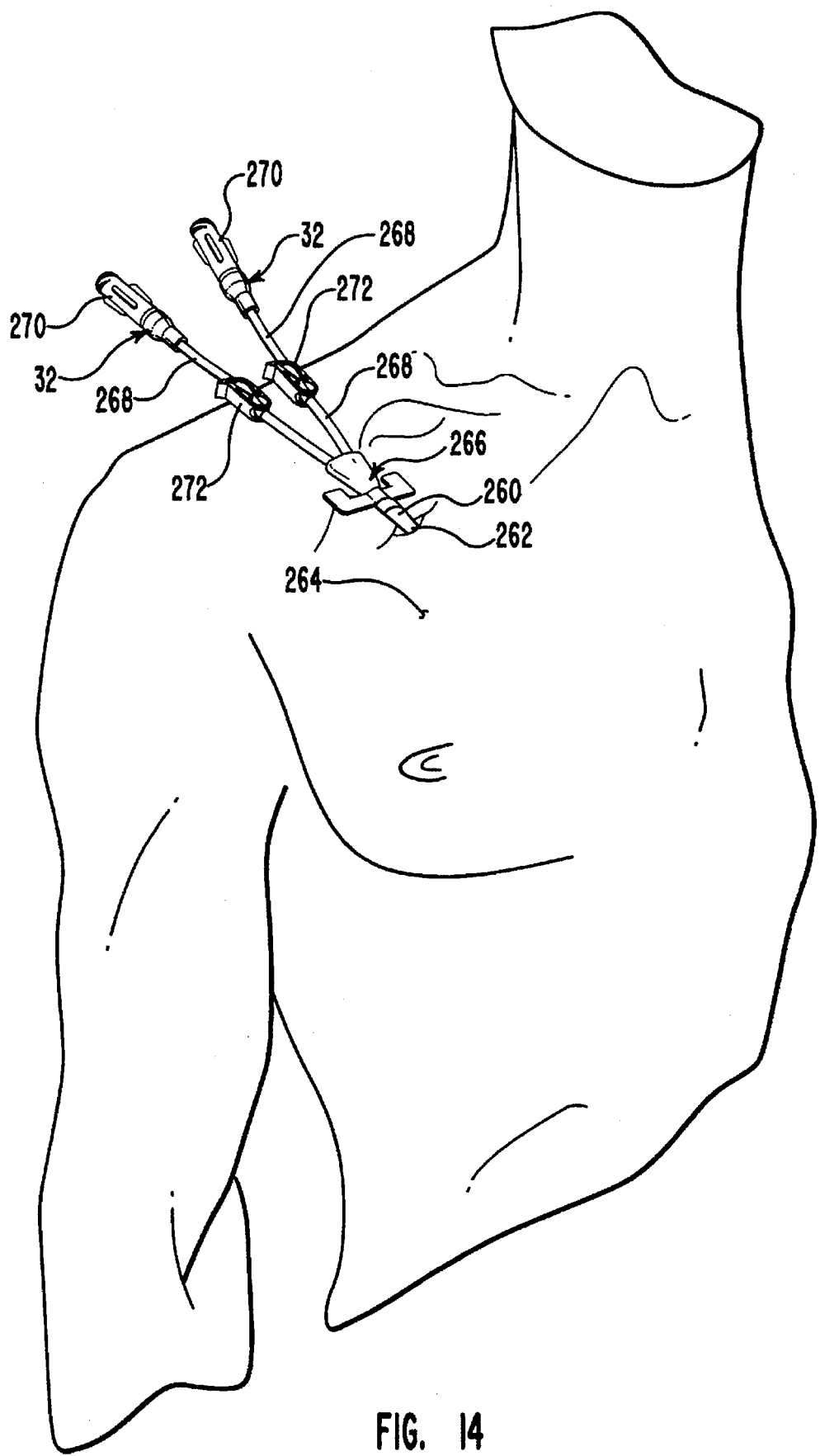
FIG. 14 is a perspective view of a proximal end of a dual lumen catheter extending from a body of a patient and having a bifurcation hub and a pair of access tubes each having a catheter termination hub secured thereto by a catheter connection system embodying teaching of the present invention.

In yet another example of how catheter connection system 32 can be used, FIG. 14 depicts a proximal end 260 of a dual lumen catheter 262 extending from chest 264 of a patient. Dual lumen catheter 262 has a bifurcation hub 266 and a pair of access tubes 268, each having a catheter termination hub 270 secured thereto by catheter connection system 32. Attached on access tubes 268 are a pair of hose clamps 272 for regulating fluid flow therein.

Illustrated in FIG. 15 is a catheter repair and extension stent 274 which is also another example of a medical device that can be used with an embodiment of catheter connection system 32. Extension stent 274 is used for splicing together sections of a broken catheter or for lengthening an existing catheter by attaching together opposing ends of distinct catheters. Extender 274 has a distal side 276 with a stem 278 extending therefrom. Positioned on stem 278 is a first engagement barb 280, a second engagement barb 282, and a locking barb 284. Extension stent 274 also has a proximal side 286 with a stem 288 extending therefrom. Positioned on stem 288 is a first engagement barb 290, a second engagement barb 292 and a locking barb 294. A passageway extends through extension stent 274 to place stem 278 and stem 288 in fluid communication.

FIG. 15 also depicts a first fastening assembly 296 for attaching a silicone catheter 298 to stem 278 and a second fastening assembly 300 for attaching a polyurethane catheter 302 to stem 278. A first fastening assembly 304 is also shown for attaching a silicone catheter 306 to stem 288 and a second fastening assembly 308 for attaching a polyurethane catheter 310 to stem 288.

The above disclosed medical devices each accommodate a fluid flow. In an alternative example, catheter connection system 32 can be used for mechanically joining a catheter to a medical tunneling device 312 as shown in FIG. 16. Tunneling device 312 does not accommodate a fluid flow but is used for threading a catheter through tissue of a patient to a desired location within the body of the patient. Medical tunneling device 312 has a pointed distal end 314 and a base 316 with a stem 318 extending therefrom. Stem 318 has a single engagement barb 320 and a single locking barb 322 positioned distal therefrom. In further distinction from stem 34, stem 318 has a cylindrical portion 324 that projects from engagement barb 320 to a distal terminus 326. FIG. 16 also illustrates a first fastening assembly 328 for attaching a silicone catheter 330 to stem 318 or a second attachment assembly 332 for attaching a polyurethane catheter 334 to stem 318.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter connection system for effecting a mechanical joinder between a medical device and a selected catheter chosen from either a first catheter or a second catheter, the first catheter being made from a first material and the second catheter being made from a second material, the second material being less pliant than the first material, the selected catheter having a body wall with an exterior surface and with an interior surface defining a longitudinally extending, fluid flow lumen, said connection system comprising:
    (a) a rigid stem attached at a proximal end thereof to the medical device, said stem having a free distal end opposite said proximal end and an exterior surface extending therebetween;
    (b) attachment means on said exterior surface of said stem for engaging the interior surface of the selected catheter when said distal end of said stem is received in the lumen of the selected catheter, and for enabling locking of the selected catheter on said stem; and
    (c) securing means operative when said distal end of said stem is received in the lumen of the selected catheter for radially, inwardly compressing a portion of the body wall of the selected catheter against a portion of said attachment means on said stem, and for interacting with said attachment means to preclude unintentional disengagement of the selected catheter from said stem, said securing means comprising a set of fastening assemblies, individual of said fastening assemblies corresponding to the first catheter and the second catheter.

2. A catheter connection system as defined in claim 1, wherein said set of fastening assemblies comprises a first fastening assembly corresponding to the first catheter, said first fastening assembly comprising:
    (a) a first locking sleeve having a proximal end, a distal end, and an interior surface defining a passageway longitudinally extending through said first locking sleeve, said interior surface of said first locking sleeve radially, inwardly compressing a portion of the body wall of the first catheter against said portion of said attachment means on said stem when said stem is received in the lumen of the first catheter and the first catheter with said stem received therein is positioned within said passageway of said first locking sleeve; and
    (b) an annular compression ring extending inwardly from said interior surface of said first locking sleeve.

3. A catheter connection system as defined in claim 2, wherein said annular compression ring is positioned at said proximal end of said first locking sleeve.

4. A catheter connection system as defined in claim 2, wherein said interior surface of said first locking sleeve further comprises a proximal shoulder sloping radially outward from said compression ring to said proximal end of said first locking sleeve to form an enlarged receiving mouth.

5. A catheter connection system as defined in claim 1, wherein the first material of the first catheter is silicone.

6. A catheter connection system as defined in claim 1, wherein the second material of the second catheter is polyurethane.

7. A catheter connection system as defined in claim 1, wherein said set of fastening assemblies comprises a second fastening assembly corresponding to the second catheter made from the second material being less pliant than the first material, said second fastening assembly comprising:
    (a) a second locking sleeve having a distal end, a proximal end, and an interior surface defining a passageway extending therebetween;
    (b) a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing a portion of the body wall of the second catheter against said portion of said attachment means on said stem when said stem is received in the lumen of the second catheter and the second catheter with said stem received therein is positioned within said passageway of said compression sleeve; and
    (c) an opposing set of radially displacable, resilient C-shaped clamps positioned at said proximal end of said second locking sleeve.

8. A catheter connection system as defined in claim 7, wherein said passageway of said compression sleeve has an inner diameter, the second catheter has a outer diameter, and said inner diameter of said passageway of said compression sleeve is at least as large as the outer diameter of the second catheter.

9. A catheter connection system as defined in claim 4, wherein said second locking sleeve further comprises an annular bracing ring extending inwardly from said interior surface of said second locking sleeve.

10. A catheter connection system as defined in claim 7, wherein said bracing ring is positioned at said distal end of said second locking sleeve.

11. A catheter connection system as defined in claim 9, wherein said compression sleeve further comprises:
    (a) a head portion having an exterior surface and a first outer diameter; and
    (b) a tail portion having a second outer diameter smaller than said first outer diameter of said head portion.

12. A catheter connection system as defined in claim 11, wherein said exterior surface of said head portion of said compression sleeve is biased against said interior surface of said locking sleeve between said C-shaped clamps and said bracing ring.

13. A catheter connection system as defined in claim 11, wherein a portion of said tail portion of said compression sleeve projects beyond said distal end of said second locking sleeve.

14. A catheter connection system as defined in claim 1, wherein said attachment means comprises:
    (a) an engagement barb radially, outwardly extending on said exterior surface of said stem and encircling said stem; and
    (b) a locking barb radially, outwardly extending on said exterior surface of said stem and encircling said stem between said engagement barb and the medical device.

15. A catheter connection system as defined in claim 14, wherein said engagement barb has a maximum outer diameter, said locking barb as a maximum outer diameter, and said maximum outer diameter of said locking barb is larger than said maximum outer diameter of said engagement barb.

16. A catheter connection system as defined in claim 14, wherein said attachment means further comprises a plurality of engagement barbs radially, outwardly extending on said exterior surface of said stem and encircling said stem.

17. A catheter connection system as defined in claim 14, wherein said locking barb further comprises:
   a) an annular distal side wall encircling said stem and radially extending outward therefrom to a first outside corner having an outer diameter,
   (b) a proximal side wall encircling said stem and radially extending outward therefrom to a second outside corner having an outer diameter larger than said outer diameter of said first outside corner, and
   (c) a frustoconical top surface encircling said stem and extending between said first outside corner and said second outside corner.

18. A catheter connection system as defined in claim 17, wherein said proximal side wall extends from said exterior surface of said stem to said second outside corner at an angle greater than 90° as measured between said proximal side wall and the longitudinal axis of said stem proximal of said proximal side wall.

19. A catheter connection system as defined in claim 1, wherein the medical device is an implantable port.

20. A catheter connection system as defined in claim 19, wherein said implantable port includes an access port with a septum.

21. A catheter connection system as defined in claim 19, wherein said implantable port includes a leaflet valve.

22. A catheter connection system as defined in claim 1, wherein the medical device is a catheter termination hub.

23. A catheter connection system as defined in claim 1, wherein the medical device is a catheter repair and extension assembly.

24. A catheter connection system as defined in claim 1, wherein the medical device is a medical tunneling instrument.

25. A catheter connection system for effecting a fluid tight coupling and a mechanical joinder between a medical device that accommodates a fluid flow and a selected catheter chosen from either a first catheter or a second catheter, the first catheter being made from a first material and the second catheter being made from a second material, the second material being less pliant than the first material, the selected catheter having a body wall with an exterior surface and with an interior surface defining a longitudinally extending, fluid flow lumen, said connection system comprising:
   (a) a rigid, tubular stem attached at a proximal end thereof in fluid communication to the medical device, said stem having a free distal end opposite said proximal end and an exterior surface extending therebetween;
   (b) attachment means on said exterior surface of said stem for engaging the interior surface of the selected catheter when said distal end of said stem is received in the lumen of the selected catheter, and for enabling locking of the selected catheter on said stem, said attachment means comprising:
      (i) an engagement barb radially, outwardly extending on said exterior surface of said stem and encircling said stem, said engagement barb having a maximum outer diameter so sized as to fit within the lumen of the selected catheter when said distal end of said stem is received in the lumen of the selected catheter; and
      (ii) a locking barb radially, outwardly extending on said exterior surface of said stem and encircling said stem between said engagement barb and the medical device, said locking barb having a maximum outer diameter that is larger than said maximum outer diameter of said engagement barb; and
   (c) securing means operative when said distal end of said stem is received in the lumen of the selected catheter for radially, inwardly compressing a portion of the body wall of the selected catheter against a portion of said attachment means on said stem, and for interacting with said attachment means to preclude unintentional disengagement of the selected catheter from said stem.

26. A catheter connection system as defined in claim 25, wherein said stem is rigid.

27. A catheter connection system as defined in claim 25, wherein said stem, engagement barb, and locking barb are each made of metal.

28. A catheter connection system as defined in claim 25, wherein said stem, engagement barb, and locking barb are each made of plastic.

29. A catheter connection system as defined in claim 25, wherein said attachment means further comprises a plurality of comparably sized engagement barbs radially, outwardly extending on said exterior surface of said stem and encircling said stem.

30. A catheter connection system as defined in claim 25, wherein said attachment means further comprises two comparably sized engagement barbs radially, outwardly extending on said exterior surface of said stem and encircling said stem.

31. A catheter connection system as defined in claim 25, wherein said attachment means further comprises three comparably sized engagement barbs radially, outwardly extending on said exterior surface of said stem and encircling said stem.

32. A catheter connection system as defined in claim 25, wherein said engagement barb is positioned at said distal end of said stem.

33. A catheter connection system as defined in claim 25, wherein said engagement barb is positioned on said stem at a distance from said distal end of said stem.

34. A catheter connection system as defined in claim 25, wherein the first material of the first catheter is silicone.

35. A catheter connection system as defined in claim 25, wherein the second material of the second catheter is polyurethane.

36. A catheter connection system as defined in claim 25, wherein a portion of said stem extends between said locking barb and said medical device.

37. A catheter connection system as defined in claim 25, wherein a portion of said stem extends between said locking barb and said engagement barb.

38. A catheter connection system as defined in claim 25, wherein said locking barb further comprises:
   (a) a proximal side wall encircling said stem and radially extending outward therefrom to an outside corner; and
   (b) a frustoconical top surface encircling said stem and extending at a slope from said outside corner of said proximal side wall to said exterior surface of said stem.

39. A catheter connection system as defined in claim 25, wherein said locking barb further comprises:
   (a) an annular distal side wall encircling said stem and radially extending outward therefrom to a first outside corner having an outer diameter;

(b) a proximal side wall encircling said stem and radially extending outward therefrom to a second outside corner having an outer diameter larger than said outer diameter of said first outside corner; and (c) a frustoconical top surface encircling said stem and extending between said first outside corner and said second outside corner.

40. A catheter connection system as defined in claim 39, wherein said proximal side wall extends from said exterior surface of said stem to said second outside corner at an angle greater than 90° as measured between said proximal side wall and the longitudinal axis of said stem proximal of said proximal side wall.

41. A catheter connection system as defined in claim 25, wherein the medical device is an access port.

42. A catheter connection system as defined in claim 25, wherein the medical device is a leaflet port.

43. A catheter connection system as defined in claim 25, wherein the medical device is a catheter termination hub.

44. A catheter connection system as defined in claim 25, wherein the medical device is a catheter repair and extension stent.

45. A catheter connection system as defined in claim 25, wherein said securing means comprises a set of fastening assemblies, individual of said fastening assemblies corresponding to the first catheter and the second catheter.

46. A catheter connection system as defined in claim 45, wherein said set of fastening assemblies comprises a first fastening assembly corresponding to the first catheter, said first fastening assembly comprising:

(a) a first locking sleeve having a proximal end, a distal end, and an interior surface defining a passageway longitudinally extending through said first locking sleeve, said interior surface of said first locking sleeve radially, inwardly compressing a portion of the body wall of the first catheter against said portion of said attachment means on said stem when said stem is received in the lumen of the first catheter and the first catheter with said stem received therein is positioned within said passageway of said first locking sleeve; and (b) an annular compression ring extending inwardly from said interior surface of said first locking sleeve.

47. A catheter connection system as defined in claim 45, wherein said set of fastening assemblies comprises a second fastening assembly corresponding to the second catheter made from the second material being less pliant than the first material, said second fastening assembly comprising:

(a) a second locking sleeve having a distal end, a proximal end, and an interior surface defining a passageway extending therebetween;

(b) a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing a portion of the body wall of the second catheter against said portion of said attachment means on said stem when said stem is received in the lumen of the second catheter and the second catheter with said stem received therein is positioned within said passageway of said compression sleeve; and (c) an opposing set of radially displacable, resilient C-shaped clamps positioned at said proximal end of said second locking sleeve.

48. A catheter connection system for effecting a fluid tight coupling and a mechanical joinder between a medical device that accommodates a fluid flow and a selected catheter chosen from either a silicone catheter or a polyurethane catheter, the selected catheter having a body wall with an exterior surface and with an interior surface defining a longitudinally extending, fluid flow lumen, said connection system comprising:

(a) a rigid, tubular stem attached at a proximal end thereof in fluid communication to the medical device, said stem having a free distal end opposite said proximal end and an exterior surface extending therebetween;

(b) attachment means on said exterior surface of said stem for engaging the interior surface of the selected catheter when said distal end of said stem is received in the lumen of the selected catheter, and for enabling locking of the selected catheter on said stem; and (c) a pair of locking sleeves comprising a first locking sleeve corresponding to the silicone catheter and a second locking sleeve corresponding to the polyurethane catheter, each of said first locking sleeve and said second locking sleeves having a distal end, a proximal end, an interior surface defining a passageway longitudinally extending through said sleeve, and an annular securement ring radially inwardly extending from said interior surface of said locking sleeve, said interior surface of said locking sleeve radially inwardly compressing a portion of the body wall of the selected catheter against a portion of said attachment means on said stem, when said stem is received in the lumen of the selected catheter and the selected catheter with said stem received therein is positioned within said passageway of said locking sleeve.

49. A catheter connection system as defined in claim 48, wherein said first locking sleeve has an exterior surface that is substantially cylindrical.

50. A catheter connection system as defined in claim 48, wherein said exterior surface of said first locking sleeve comprises:

(a) a first cylindrical portion positioned at said distal end and having an outer diameter;

(b) a second cylindrical portion positioned at said proximal end and having an outer diameter larger than said outer diameter of said first cylindrical portion; and (c) a frustoconical shoulder extending between said first cylindrical portion and said second cylindrical portion.

51. A catheter connection system as defined in claim 48, wherein said interior surface of said first locking sleeve is substantially cylindrical.

52. A catheter connection system as defined in claim 49, wherein said annular securement ring of said first locking sleeve comprises a compression ring positioned at said proximal end of said first locking sleeve.

53. A catheter connection system as defined in claim 52, wherein said interior surface of said first locking sleeve further comprises a proximal shoulder sloping radially outward from said compression ring to said proximal end of said first locking sleeve to form an enlarged receiving mouth.

54. A catheter connection system as defined in claim 49, wherein said first locking sleeve is rigid.

55. A catheter connection system as defined in claim 49, wherein said first locking sleeve is made of plastic.

56. A catheter connection system as defined in claim 49, wherein said first locking sleeve is made of metal.

57. A catheter connection system as defined in claim 49, wherein said second locking sleeve is rigid.

58. A catheter connection system as defined in claim 49, wherein said second locking sleeve is made of plastic.

59. A catheter connection system as defined in claim 49, wherein said second locking sleeve is made of metal.

60. A catheter connection system as defined in claim 49, wherein said second locking sleeve further comprises a pliable compression sleeve longitudinally disposed within said passageway of said second locking sleeve and having an interior surface defining a passageway longitudinally extending therethrough.

61. A catheter connection system as defined in claim 60, wherein said annular securement ring of said second locking sleeve comprises an annular attachment ridge positioned on said interior surface of said second locking sleeve at said proximal end thereof.

62. A catheter connection system as defined in claim 61, wherein said proximal end of said second locking sleeve includes a plurality of slots extending through said proximal end and through said attachment ridge to enable said attachment ridge to radially expand under a radial force.

63. A catheter connection system as defined in claim 61, wherein said proximal end of said second locking sleeve includes a slot extending through said proximal end and through said attachment ridge to enable said attachment ridge to radially expand under a radial force.

64. A catheter connection system as defined in claim 61, wherein said second locking sleeve further comprises an annular bracing ring extending inwardly from said interior surface of said second locking sleeve at said distal end thereof.

65. A catheter connection system as defined in claim 64, wherein said compression sleeve comprises:
    (a) a head portion having an exterior surface and a first outer diameter; and
    (b) a tail portion having a second outer diameter smaller than said first outer diameter of said head portion.

66. A catheter connection system as defined in claim 65, wherein said interior surface of said head portion is biased against said interior surface of said second locking sleeve between said attachment ridge and said bracing ring.

67. A catheter connection system as defined in claim 66, wherein a portion of said tail portion of said compression sleeve projects beyond said distal end of said second locking sleeve.

68. A catheter connection system as defined in claim 65, wherein said exterior surface of said head portion of said compression sleeve is secured by an adhesive to said interior surface of said locking sleeve.

69. A catheter connection system as defined in claim 48, wherein said attachment means comprises:
    (a) an engagement barb radially, outwardly extending on said exterior surface of said stem and encircling said stem; and
    (b) a locking barb radially, outwardly extending on said exterior surface of said stem and encircling said stem between said engagement barb and the medical device.

70. A catheter connection system as defined in claim 69, wherein said engagement barb has a maximum outer diameter and said locking barb as a maximum outer diameter that is larger than said maximum outer diameter of said engagement barb.

71. A catheter connection system as defined in claim 69, wherein said attachment means further comprises a plurality of engagement barbs radially, outwardly extending on said exterior surface of said stem and encircling said stem.

72. A catheter connection system for effecting a fluid tight coupling and a mechanical joinder between a medical device that accommodates a fluid flow and a selected catheter chosen from either a silicone catheter or a polyurethane catheter, the selected catheter having a body wall with an exterior surface and with an interior surface defining a longitudinally extending, fluid flow lumen, said connection system comprising:
    (a) a rigid, tubular stem attached at a proximal end thereof in fluid communication to the medical device, said stem having a free distal end opposite said proximal end and an exterior surface extending therebetween;
    (b) a plurality of comparably configured engagement barbs radially, outwardly extending on said exterior surface of said stem and encircling said stem, said engagement barbs having a maximum outer diameter so sized as to fit within the lumen of the selected catheter when said distal end of said stem is received in the lumen of the selected catheter;
    (c) a locking barb radially, outwardly extending on said exterior surface of said stem and encircling said stem between said engagement barbs and the medical device, said locking barb having a maximum outer diameter that is larger than said maximum outer diameter of said engagement barbs; and
    (d) a set of fastening assemblies, individual of said fastening assemblies corresponding to each one of the polyurethane catheter and the silicone catheter, said set of fastening assemblies comprising:
        (i) a first fastening assembly corresponding to the silicone catheter, said first fastening assembly comprising:
            (A) a first locking sleeve having a proximal end, a distal end, and an interior surface defining a passageway longitudinally extending through said first locking sleeve, said interior surface of said first locking sleeve radially, inwardly compressing a portion of the body wall of the silicone catheter against said locking barb on said stem when said stem is received in the lumen of the silicone catheter and the silicone catheter with said stem received therein is positioned within said passageway of said first locking sleeve; and
            (B) an annular compression ring extending inwardly from said interior surface of said first locking sleeve to interact with said locking barb; and
        (ii) a second fastening assembly corresponding to the polyurethane catheter, said second fastening assembly comprising:
            (A) a second locking sleeve having a distal end, a proximal end, and an interior surface defining a passageway extending through said second locking sleeve;
            (B) a pliable compression sleeve longitudinally disposed within said passageway of said second locking sleeve and having an interior surface defining a passageway longitudinally extending therethrough, said interior surface of said compression sleeve radially, inwardly compressing a portion of the body wall of the polyurethane catheter against said engagement barbs on said stem when said stem is received in the lumen of the polyurethane catheter and the polyurethane catheter with said stem received therein is positioned within said passageway of said compression sleeve; and
            (C) an opposing set of radially displacable, resilient C-shaped clamps positioned at said proximal end of said second locking sleeve to grasp said locking barb.

73. A catheter connection system as defined in claim 72, wherein said plurality of engagement barbs are adjacently disposed on said distal end of said stem.

74. A catheter connection system as defined in claim 72, wherein a portion of said stem extends between said engagement barbs and said distal end of said stem.

75. A catheter connection system as defined in claim 72, wherein said locking barb further comprises:
   (a) an annular distal side wall encircling said stem and radially extending outward therefrom to a first outside corner having an outer diameter;
   (b) a proximal side wall encircling said stem and radially extending outward therefrom to a second outside corner having an outer diameter larger than said outer diameter of said first outside corner; and
   (c) a frustoconical top surface encircling said stem and extending between said first outside corner and said second outside corner.

76. A catheter connection system as defined in claim 75, wherein said proximal side wall extends from said exterior surface of said stem to said second outside corner at an angle greater than 90° as measured between said proximal side wall and the longitudinal axis of said stem proximal of said proximal side wall.

77. A catheter connection system as defined in claim 72, wherein said annular compression ring is positioned at said proximal end of said first locking sleeve.

78. A catheter connection system as defined in claim 72, wherein said annular compression ring of the first locking sleeve is longitudinally positioned within said passageway so as to reside between said locking barb and the medical device when said stem is received in the lumen of the silicone catheter and the silicone catheter with said stem received therein is positioned within said passageway of said first locking sleeve.

79. A catheter connection system as defined in claim 72, wherein said compression ring of said first fastening assembly has an inner diameter that is larger than said maximum outer diameter of said locking barb.

80. A catheter connection system as defined in claim 72, wherein said compression ring of said first fastening assembly has an inner diameter, the silicone catheter has an outer diameter, and said inner diameter of said compression ring is larger than the outer diameter of the silicone catheter.

81. A catheter connection system as defined in claim 72, wherein the lumen of the silicone catheter has an inside diameter that is smaller than said maximum outer diameter of said locking barb.

82. A catheter connection system as defined in claim 72, wherein said interior surface of said first locking sleeve radially, inwardly compresses a portion of the body wall of the silicone catheter against said engagement barbs on said stem when said stem is received in the lumen of the silicone catheter and the silicone catheter with said stem received therein is positioned within said passageway of said first locking sleeve.

83. A catheter connection system as defined in claim 72, wherein said second locking sleeve further comprises an annular bracing ring extending inwardly from said interior surface of said second locking sleeve at said distal end thereof.

84. A catheter connection system as defined in claim 83, wherein said compression sleeve comprises:
   (a) a head portion having an exterior surface and a first outer diameter; and
   (b) a tail portion having a second outer diameter smaller than said first outer diameter of said head portion.

85. A catheter connection system as defined in claim 84, wherein a portion of said tail portion of said compression sleeve projects beyond said distal end of said second locking sleeve.

86. A catheter connection system as defined in claim 84, wherein said exterior surface of said head portion is biased against said interior surface of said locking sleeve between said C-shaped clamps and said bracing ring.

87. A catheter connection system as defined in claim 72, wherein each of said C-shaped clamps comprises:
   (a) an arm longitudinally positioned at said proximal end of said second locking sleeve; and
   (b) an attachment ridge radially inwardly extending from said arm.

88. A catheter connection system as defined in claim 87, wherein said attachment ridge of said C-shaped clamp is longitudinally positioned on said arm so as to reside between said locking barb and said medical device when said stem is received in the lumen of the polyurethane catheter and the polyurethane catheter with said stem received therein is positioned within said passageway of said second locking sleeve.

89. A catheter connection system as defined in claim 72, wherein said passageway of said compression sleeve has an inner diameter, the polyurethane catheter has a outer diameter, and the inner diameter of the compression sleeve is larger than the outer diameter of the polyurethane catheter.

90. A catheter connection system as defined in claim 72, wherein said C-shaped clamps have an inner diameter that is smaller than said maximum outer diameter of said locking barb.

91. A catheter connection system as defined in claim 72, wherein the lumen of the polyurethane catheter has an inside diameter that is smaller than said maximum outer diameter of said engagement barbs.

92. A catheter connection system as defined in claim 72, wherein said locking barb is longitudinally positioned on said stem so that said C-shaped clamps are positioned between said locking barb and the medical device when said stem is received in the lumen of the polyurethane catheter and the polyurethane catheter with said stem received therein is positioned within said passageway of said compression sleeve.

93. A catheter connection system as defined in claim 72, wherein the medical device is an implantable port.

94. A catheter connection system as defined in claim 93, wherein said port includes an access port with a septum.

95. A catheter connection system as defined in claim 93, wherein said port includes a leaflet valve.

96. A catheter connection system as defined in claim 72, wherein the medical device is a catheter termination hub.

97. A catheter connection system as defined in claim 72, wherein the medical device is a catheter repair and extension stent.

98. A catheter connection system for mechanically joining a medical tunneling instrument to a selected catheter chosen from either a silicone catheter or a polyurethane catheter, the selected catheter having a body wall with an interior surface defining a longitudinally extending, fluid flow lumen, said connection system comprising:
   (a) a rigid, tubular stem attached at a proximal end thereof to the tunneling instrument, said stem having a free distal end opposite said proximal end and an exterior surface extending therebetween;
   (b) attachment means on said exterior surface of said stem for engaging the interior surface of the selected catheter when said distal end of said stem is received in the lumen of the selected catheter, and for enabling locking of the selected catheter on said stem; and
   (c) securing means operative when said distal end of said stem is received in the lumen of the selected catheter for radially, inwardly compressing a portion of the body wall of the selected catheter against a portion of said attachment means on said stem, and for interacting with said attachment means to preclude unintentional disengagement of the selected catheter from said stem, said securing means comprising a set of fastening assemblies, individual of said fastening assemblies corresponding to the silicone catheter and the polyurethane catheter.

99. A catheter connection system as defined in claim 98, wherein said set of fastening assemblies comprises a second fastening assembly corresponding to the polyurethane catheter, said second fastening assembly comprising:

(a) a second locking sleeve having a distal end, a proximal end, and an interior surface defining a passageway extending therebetween;

(b) a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing a portion of the body wall of the polyurethane catheter against a portion of said attachment means on said stem when said stem is received in the lumen of the polyurethane catheter and the polyurethane catheter with said stem received therein is positioned within said passageway of said compression sleeve; and (c) an opposing set of radially displacable, resilient C-shaped clamps positioned at said proximal end of said second locking sleeve.

100. A catheter connection system as defined in claim 98, wherein said set of fastening assemblies comprises a first fastening assembly corresponding to the silicone catheter, said first fastening assembly comprising:

(a) a first locking sleeve having a distal end, a proximal end, and an interior surface defining a passageway longitudinally extending through said first locking sleeve, said interior surface of said first locking sleeve radially, inwardly compressing a portion of the body wall of the silicone catheter against a portion of said attachment means on said stem when said stem is received in the lumen of the silicone catheter and the silicone catheter with said stem received therein is positioned within said passageway of said first locking sleeve; and (b) an annular compression ring extending inwardly from said interior surface of said first locking sleeve.

101. A catheter connection system as defined in claim 98, wherein said attachment means comprises:

(a) an engagement barb radially, outwardly extending on said exterior surface of said stem and encircling said stem; and (b) a locking barb radially, outwardly extending on said exterior surface of said stem and encircling said stem between said engagement barb and the medical device.

102. A catheter connection system as defined in claim 101, wherein said engagement barb has a maximum outer diameter, said locking barb as a maximum outer diameter, and said maximum outer diameter of said locking barb is larger than said maximum outer diameter of said engagement barb.

103. A catheter connection system as defined in claim 101, wherein said attachment means further comprises a plurality of engagement barbs radially, outwardly extending on said exterior surface of said stem and encircling said stem.

104. A catheter connection system for effecting a fluid tight coupling and a mechanical joinder between a medical device that accommodates a fluid flow and a polyurethane catheter, the polyurethane catheter having a body wall with an exterior surface and with an interior surface defining a longitudinally extending, fluid flow lumen, said connection system comprising:

(a) a rigid, tubular stem attached at a proximal end thereof in fluid communication to the medical device, said stem having a free distal end opposite said proximal end and an exterior surface extending therebetween;

(b) an engagement barb radially, outwardly extending on said exterior surface of said stem and encircling said stem, said engagement barb having a maximum outer diameter so sized as to fit within the lumen of the polyurethane catheter when said distal end of said stem is received in the lumen of the polyurethane catheter;

(c) a locking barb radially, outwardly extending on said exterior surface of said stem and encircling said stem between said engagement barb and the medical device, said locking barb having a maximum outer diameter that is larger than said maximum outer diameter of said engagement barb; and (d) a fastening assembly comprising:

(i) a locking sleeve having a distal end, a proximal end, and an interior surface defining a passageway extending therebetween;

(ii) a pliable compression sleeve longitudinally disposed within said passageway of said locking sleeve and having an interior surface defining a passageway longitudinally extending therethrough, said interior surface of said compression sleeve radially, inwardly compressing a portion of the body wall of the polyurethane catheter against said engagement barb on said stem when said stem is received in the lumen of the polyurethane catheter and the polyurethane catheter with said stem received therein is positioned within said passageway of said compressive sleeve; and (iii) an opposing set of radially displacable, resilient C-shaped clamps positioned at said proximal end of said second locking sleeve to grasp said locking barb.

105. A catheter connection system as defined in claim 104, wherein said locking sleeve further comprises an annular bracing ring extending inwardly from said interior surface of said locking sleeve.

106. A catheter connection system as defined in claim 105, wherein said bracing ring is positioned at said distal end of said locking sleeve.

107. A catheter connection system as defined in claim 105, wherein said compression sleeve comprises:

(a) a head portion having an exterior surface and a first outer diameter; and (b) a tail portion having a second outer diameter smaller than said first outer diameter of said head portion.

108. A catheter connection system as defined in claim 107, wherein said exterior surface of said head portion is biased against said interior surface of said locking sleeve between said C-shaped clamps and said bracing ring.

109. A catheter connection system as defined in claim 107, wherein a portion of said tail portion of said compression sleeve extends beyond said distal end of said second locking sleeve.

110. A catheter connection system as defined in claim 104, wherein said C-shaped clamps having an inner diameter that is smaller than said maximum outer diameter of said locking barb.

111. A catheter connection system as defined in claim 104, wherein said locking barb is longitudinally positioned on said stem so that said C-shaped clamps are positioned between said locking barb and the medical device when said stem is received in the lumen of the polyurethane catheter and the polyurethane catheter with said stem received therein is positioned within said passageway of said compression sleeve.

112. A method for effecting a mechanical joinder between a medical device and a catheter, the method comprising the steps of:
 (a) choosing a selected catheter from either a silicone catheter or a polyurethane catheter, said selected catheter having a body wall with an exterior surface and with an interior surface defining a longitudinally extending, fluid flow lumen, said lumen being sized to receive a rigid, tubular stem attached at a proximal end thereof to the medical device;
 (b) positioning said tubular stem in said lumen of said selected catheter, said tubular stem having a free distal end opposite said proximal end and an exterior surface extending therebetween, said stem further comprising an attachment means on said exterior surface of said stem for engaging said interior surface of said selected catheter when said distal end of said stem is received in said lumen of said selected catheter, and for enabling locking of said selected catheter on said stem;
 (c) picking a selected fastening assembly from a pair of fastening assemblies including a first fastening assembly corresponding to said silicone catheter and a second fastening assembly corresponding to said polyurethane catheter, said selected fastening assembly being chosen to correspond to said selected catheter and comprising a locking sleeve having a distal end, a proximal end, an interior surface defining a passageway longitudinally extending through said sleeve, and an annular securement ring radially inwardly extending from said interior surface of said locking sleeve; and
 (d) placing said stem positioned in said lumen of said selected catheter within said passageway of said locking sleeve, said interior surface of said locking sleeve radially, inwardly compressing a portion of said body wall of said selected catheter against a portion of said attachment means on said stem.

113. A method as defined in claim 112, wherein said attachment means comprises:
 (a) an engagement barb encircling and radially, outwardly extending on said exterior surface of said stem and having an outer diameter; and
 (b) a locking barb encircling and radially, outwardly extending on said exterior surface of said stem and having an outer diameter larger than said outer diameter of said engagement barb.

114. A method as defined in claim 113, wherein said positioning step includes said engagement barb being received within said lumen of said selected catheter.

115. A method as defined in claim 113, wherein said positioning step includes both said engagement barb and said locking barb being received within said lumen of said selected catheter.

116. A method as defined in claim 113, wherein said placing step includes said securement ring being positioned between said locking barb and the medical device.

117. A method as defined in claim 113, wherein said placing step includes positioning said interior surface of said locking sleeve over said locking barb to compress a portion of said body wall of said selected catheter against said locking barb.

118. A method as defined in claim 113, wherein said placing step includes positioning said interior surface of said locking sleeve over said engagement barb to compress a portion of said body wall of said selected catheter against said engagement barb.

119. A method as defined in claim 112, wherein the medical device accommodates a fluid flow and is attached in fluid communication with said stem.

* * * * *